US012023384B2

(12) United States Patent
Saint-Remy et al.

(10) Patent No.: US 12,023,384 B2
(45) Date of Patent: Jul. 2, 2024

(54) IMMUNOGENIC PEPTIDES COMPRISING AN MHC CLASS II T CELL EPITOPE AND A REDOX MOTIF

(71) Applicant: IMCYSE SA, Liége (BE)

(72) Inventors: Jean-Marie Saint-Remy, Grez-Doiceau (BE); Vincent Carlier, Enines (BE); Luc Vander Elst, Obaix (BE); David Burkhart, Victor, MT (US)

(73) Assignee: IMCYSE SA, Liége (BE)

( * ) Notice: Subject to any disclaimer, the term of this patent is extended or adjusted under 35 U.S.C. 154(b) by 0 days.

(21) Appl. No.: 16/892,588

(22) Filed: Jun. 4, 2020

(65) Prior Publication Data
US 2020/0397911 A1 Dec. 24, 2020

Related U.S. Application Data

(63) Continuation of application No. 15/516,045, filed as application No. PCT/EP2015/074063 on Oct. 16, 2015, now abandoned.

(30) Foreign Application Priority Data

Oct. 17, 2014 (GB) .................................. 1418433

(51) Int. Cl.
C07K 2/00 (2006.01)
A61K 39/00 (2006.01)
A61K 39/385 (2006.01)
A61K 47/64 (2017.01)
A61P 25/00 (2006.01)
A61P 37/02 (2006.01)
C07K 14/47 (2006.01)
C07K 14/74 (2006.01)

(52) U.S. Cl.
CPC ........ A61K 47/646 (2017.08); A61K 39/0008 (2013.01); A61K 39/385 (2013.01); A61P 25/00 (2018.01); A61P 37/02 (2018.01); C07K 14/4713 (2013.01); C07K 14/70539 (2013.01); A61K 2039/572 (2013.01); A61K 2039/6031 (2013.01); A61K 2039/64 (2013.01)

(58) Field of Classification Search
None
See application file for complete search history.

(56) References Cited

U.S. PATENT DOCUMENTS

| 4,599,231 | A | 7/1986 | Milich et al. |
| 4,886,782 | A | 12/1989 | Good et al. |
| 5,433,948 | A | 7/1995 | Thomas et al. |
| 5,552,142 | A | 9/1996 | Thomas et al. |
| 5,589,175 | A | 12/1996 | Vahlne et al. |
| 5,633,234 | A | 5/1997 | August et al. |
| 5,736,142 | A | 4/1998 | Sette et al. |
| 5,770,202 | A | 6/1998 | Thomas et al. |
| 5,773,002 | A | 6/1998 | Thomas et al. |
| 5,863,528 | A | 1/1999 | Hawley et al. |
| 6,399,383 | B1 | 6/2002 | Apt et al. |
| 6,602,509 | B1 | 8/2003 | Saint-Remy et al. |
| 6,656,471 | B1 | 12/2003 | Sastry et al. |
| 6,759,046 | B1 | 7/2004 | Gaudernack et al. |
| 7,157,089 | B1 | 1/2007 | Mizzen et al. |
| 7,306,804 | B2 | 12/2007 | Sastry et al. |
| 7,780,882 | B2 | 8/2010 | Chang et al. |
| 8,999,346 | B2 | 4/2015 | Saint-Remy |
| 9,044,507 | B2 | 6/2015 | Saint-Remy |
| 9,248,171 | B2 | 2/2016 | Saint-Remy |
| 9,249,202 | B2 | 2/2016 | Saint-Remy |
| 9,394,517 | B2 | 7/2016 | Saint-Remy |
| 9,861,661 | B2 | 1/2018 | Saint-Remy |
| 10,023,847 | B2 | 7/2018 | Saint-Remy |
| 10,617,748 | B2 | 4/2020 | Saint-Remy |
| 10,662,232 | B2 | 5/2020 | Saint-Remy |
| 10,729,791 | B2 | 8/2020 | Saint-Remy et al. |
| 10,808,016 | B2 | 10/2020 | Vander Elst et al. |
| 10,899,795 | B2 | 1/2021 | Saint-Remy |
| 10,982,196 | B2 | 4/2021 | Saint-Remy |
| 11,193,114 | B2 | 12/2021 | Saint-Remy |
| 11,226,332 | B2 | 1/2022 | Saint-Remy et al. |
| 11,407,795 | B2 | 8/2022 | Vander Elst et al. |
| 11,485,768 | B2 | 11/2022 | Vander Elst |
| 2003/0049723 | A1 | 3/2003 | Zhang et al. |
| 2003/0104570 | A1 | 6/2003 | Cabezon et al. |
| 2003/0129205 | A1 | 7/2003 | Saint-Remy et al. |
| 2003/0152581 | A1 | 8/2003 | Saint-Remy et al. |
| 2004/0077045 | A1 | 4/2004 | Zhang et al. |
| 2005/0032039 | A1 | 2/2005 | Sastry et al. |
| 2005/0107256 | A1 | 5/2005 | Barnwell et al. |

(Continued)

FOREIGN PATENT DOCUMENTS

WO  WO-0029008 A2  5/2000
WO  WO-0155393 A2  8/2001

(Continued)

OTHER PUBLICATIONS

Kortemme, T., et al. Biochemistry;35:14503-14511 (Year: 1996).*
Abrahimians, E.M., et al., "MHC Class II-Restricted Epitopes Containing an Oxidoreductase Activity Prompt CD4+ T Cells with Apoptosis-Inducing Properties," Frontiers in Immunology, 6:1-5, Frontiers Research Foundation, Switzerland (Sep. 2015).
Abrahimians, E.M., et al., "Thioreductase-Containing Epitopes Inhibit the Development of Type 1 Diabetes in the NOD Mouse Model," Frontiers in Immunology, 7:1-10, Frontiers Research Foundation, Switzerland (Mar. 2016).
Aleksza, M., et al., "Altered Cytokine Expression of Peripheral Blood Lymphocytes in Polymyositis and Dermatomyositis," Annals of the Rheumatic Diseases, 64(10):1485-1489, BMJ, England (Oct. 2005).

(Continued)

Primary Examiner — G. R. Ewoldt
(74) Attorney, Agent, or Firm — Nixon & Vanderhye, PC

(57) ABSTRACT

The invention relates to isolated immunogenic peptides comprising a MHC class II T cell epitope, and immediately adjacent or separated from said epitope a H-X(0,2)-C-X(2)-[CST] or [CST]-X(2)-C-X(0,2)-H redox motif.

10 Claims, 1 Drawing Sheet
Specification includes a Sequence Listing.

(56) References Cited

U.S. PATENT DOCUMENTS

| | | |
|---|---|---|
| 2005/0196386 A1 | 9/2005 | Blazar et al. |
| 2005/0202044 A1 | 9/2005 | Mizzen et al. |
| 2006/0182763 A1 | 8/2006 | Kim et al. |
| 2006/0211091 A1 | 9/2006 | Zhang et al. |
| 2006/0216301 A1 | 9/2006 | Tahara et al. |
| 2006/0269561 A1 | 11/2006 | Paterson et al. |
| 2007/0160620 A1 | 7/2007 | Mizzen et al. |
| 2007/0184023 A1 | 8/2007 | Rasmussen et al. |
| 2008/0176247 A1 | 7/2008 | Chou et al. |
| 2009/0012004 A1 | 1/2009 | Sette et al. |
| 2010/0033088 A1 | 2/2010 | Hwang et al. |
| 2010/0068193 A1 | 3/2010 | Brunsvig et al. |
| 2010/0183652 A1 | 7/2010 | Page et al. |
| 2010/0203083 A1 | 8/2010 | Lux et al. |
| 2010/0303866 A1 | 12/2010 | Saint-Remy |
| 2010/0330088 A1 | 12/2010 | Saint-Remy |
| 2011/0002903 A1 | 1/2011 | Saint-Remy |
| 2011/0110964 A1 | 5/2011 | Saint-Remy |
| 2011/0111395 A1 | 5/2011 | Saint-Remy |
| 2011/0111502 A1 | 5/2011 | Saint-Remy |
| 2012/0009678 A1 | 1/2012 | Saint-Remy |
| 2013/0095133 A1 | 4/2013 | Klatzmann et al. |
| 2013/0259885 A1 | 10/2013 | Saint-Remy |
| 2014/0186297 A1 | 7/2014 | Saint-Remy |
| 2014/0370044 A1 | 12/2014 | Saint-Remy |
| 2014/0377299 A1 | 12/2014 | Saint-Remy |
| 2015/0110821 A1 | 4/2015 | Saint-Remy |
| 2015/0125536 A1 | 5/2015 | Santamaria |
| 2015/0216901 A1 | 8/2015 | Saint-Remy |
| 2016/0091492 A1 | 3/2016 | Saint-Remy et al. |
| 2016/0108103 A1 | 4/2016 | Saint-Remy |
| 2016/0194367 A1 | 7/2016 | Saint-Remy |
| 2016/0250255 A1 | 9/2016 | Saint-Remy et al. |
| 2016/0339121 A1 | 11/2016 | Saint-Remy et al. |
| 2017/0100466 A1 | 4/2017 | Saint-Remy |
| 2018/0228912 A1 | 8/2018 | Saint-Remy et al. |
| 2018/0258154 A1 | 9/2018 | Saint-Remy et al. |
| 2018/0346887 A1 | 12/2018 | Saint-Remy |
| 2019/0106477 A1 | 4/2019 | Vander |
| 2019/0352348 A1 | 11/2019 | Vander Elst et al. |
| 2020/0103407 A1 | 4/2020 | Saint-Remy et al. |
| 2020/0179499 A1 | 6/2020 | Saint-Remy |
| 2020/0270331 A1 | 8/2020 | Saint-Remy |
| 2020/0317742 A1 | 10/2020 | Saint-Remy |
| 2020/0397911 A1 | 12/2020 | Saint-Remy |
| 2020/0407406 A1 | 12/2020 | Vander Elst et al. |
| 2021/0188913 A1 | 6/2021 | Saint-Remy |
| 2021/0401976 A1 | 12/2021 | Erak |
| 2022/0119778 A1 | 4/2022 | Saint-Remy |
| 2022/0288179 A1 | 9/2022 | Erak |
| 2022/0411476 A1 | 12/2022 | Vander Elst et al. |
| 2023/0113747 A1 | 4/2023 | Erak |

FOREIGN PATENT DOCUMENTS

| | | |
|---|---|---|
| WO | WO-0170263 A1 | 9/2001 |
| WO | WO-0200892 A1 | 1/2002 |
| WO | WO-02095051 A2 | 11/2002 |
| WO | WO-02097070 A1 | 12/2002 |
| WO | WO-03072731 A2 | 9/2003 |
| WO | WO-2004024766 A1 | 3/2004 |
| WO | WO-2005012502 A2 | 2/2005 |
| WO | WO-2005037190 A2 | 4/2005 |
| WO | WO-2005039613 A1 | 5/2005 |
| WO | WO-2005042575 A2 | 5/2005 |
| WO | WO-2005086781 A2 | 9/2005 |
| WO | WO-2006009920 A2 | 1/2006 |
| WO | WO-2007027954 A2 | 3/2007 |
| WO | WO-2007135684 A2 | 11/2007 |
| WO | WO-2008017517 A1 | 2/2008 |
| WO | WO-2009042215 A2 | 4/2009 |
| WO | WO-2009042215 A3 | 7/2009 |
| WO | WO-2009100505 A1 | 8/2009 |
| WO | WO-2009101204 A2 | 8/2009 |
| WO | WO-2009101205 A2 | 8/2009 |
| WO | WO-2009101206 A2 | 8/2009 |
| WO | WO-2009101207 A1 | 8/2009 |
| WO | WO-2009101208 A2 | 8/2009 |
| WO | WO-2009106073 A2 | 9/2009 |
| WO | WO-2010115046 A2 | 10/2010 |
| WO | WO-2011-120994 A1 | 10/2011 |
| WO | WO-2012069568 A2 | 5/2012 |
| WO | WO-2013113076 A1 | 8/2013 |
| WO | WO-2013121296 A1 | 8/2013 |
| WO | WO-2014191432 A1 | 12/2014 |
| WO | WO-2015063176 A1 | 5/2015 |
| WO | WO-2015063616 A2 | 5/2015 |
| WO | WO-2016059236 A1 | 4/2016 |

OTHER PUBLICATIONS

Aley, S.B. and Gillin, F.D., "Giardia Lamblia: Post-Translational Processing and Status of Exposed Cysteine Residues in TSA 417, A Variable Surface Antigen," Experimental Parasitology, 77(3):295-305, Academic Press, United States (Nov. 1993).

Ali-Khan, N., et al., "Overview of Proteome Analysis," Current Protocols in Protein Science, 30(1):22.1.1-22.1.19, Hoboken, NJ : Wiley Interscience, United States (Dec. 2002).

Apostolou, I., et al., "Evidence for Two Subgroups of CD4-CD8- NKT Cells With Distinct TCR Alpha Beta Repertoires and Differential Distribution in Lymphoid Tissues," Journal of Immunology, 165(5):2481-2490, American Association of Immunologists, United States (Sep. 2000).

Appella, E., et al., "Analysis of the Structure of Naturally Processed Peptides Bound by Class I and Class II Major Histocompatibility Complex Molecules," EXS, 73:105-119, Birkhäuser Verlag, Switzerland (1995).

Arunachalam, B., et al., "Enzymatic Reduction of Disulfide Bonds in Lysosomes: Characterization of a Gamma-interferon-inducible Lysosomal Thiol Reductase (GILT)," Proceedings of the National Academy of Sciences of the United States of America, 97(2):745-750, National Academy of Sciences, United States (Jan. 2000).

Ascherio, A., "Environmental Factors in Multiple Sclerosis," Expert Review of Neurotherapeutics, 13(12 Suppl):3-9, Taylor & Francis, England (Dec. 2013).

Azoury-Ziadeh, R., et al., "T-Helper Epitopes Identified Within the E6 Transforming Protein of Cervical Cancer-Associated Human Papillomavirus Type 16," Viral Immunology, 12(4):297-312, Mary Ann Liebert, Inc., United States (1999).

Balato, A., et al., "Natural Killer T Cells: an Unconventional T-Cell Subset With Diverse Effector and Regulatory Functions," The Journal of Investigative Dermatology, 129(7):1628-1642, Elsevier, United States (Jul. 2009).

Batten, P., et al., "Immune Response to Stem Cells and Strategies to Induce Tolerance," Philosophical Transactions of the Royal Society of London. Series B, Biological Sciences, 362(1484):1343-1356, Royal Society, England (Aug. 2007).

Boisgerault, F., et al., "Differential Roles of Direct and Indirect Allorecognition Pathways in the Rejection of Skin and Corneal Transplants, " Transplantation, 87(1):16-23, Lippincott Williams & Wilkins, United States (Jan. 2009).

Bolivar, J., et al., "Molecular Cloning of a Zinc Finger Autoantigen Transiently Associated With Interphase Nucleolus and Mitotic Centromeres and Midbodies. Orthologous Proteins With Nine CXXC Motifs Highly Conserved From Nematodes to Humans," The Journal of Biological Chemistry, 274(51):36456-36464, American Society for Biochemistry and Molecular Biology, United States (Dec. 1999).

Bower, M.S., et al., "Two Members of the Thioredoxin-h Family Interact With the Kinase Domain of a *Brassica S* Locus Receptor Kinase," The Plant Cell, 8(9): 1641-1650, American Society for Biochemistry and Molecular Biology, United States (Sep. 1996).

Braun, M.Y. et al., "Acute Rejection in the Absence of Cognate Recognition of Allograft by T Cells," Journal of Immunology, 166(8):4879-4883, American Association of Immunologists, United States (Apr. 2001).

(56) References Cited

OTHER PUBLICATIONS

Brinks, V., et al., "Immunogenicity of Therapeutic Proteins: The Use of Animal Models," Pharmaceutical Research, 28(10):2379-2385, Kluwer Academic/Plenum Publishers, United States (Oct. 2011).
Brinster, C. and Shevach, E.M., "Bone Marrow-Derived Dendritic Cells Reverse the Anergic State of CD4+CD25+ T Cells without Reversing Their Suppressive Function," Journal of Immunology, 175(11):7332-7340, American Association of Immunologists, United States (Dec. 2005).
Brinster, C. and Shevach, E.M., "Costimulatory Effects of IL-1 on the Expansion/differentiation of CD4+CD25+Foxp3+ and CD4+CD25+Foxp3-T Cells," Journal of Leukocyte Biology, 84(2):480-487, Wiley on behalf of the Society for Leukocyte Biology, United States (Aug. 2008).
Cao, O., et al., "Prevention of Gene Transfer-Induced Inhibitor Formation by Nasal Administration of Human F.IX T Cell Epitope in a Murine Model of Hemophilia B," Blood, 104(11):414, Nov. 2004).
Capon, D.J. and Ward, R.H., "The CD4-gp120 Interaction and Aids Pathogenesis," Annual Review of Immunology, 9:649-678, Annual Reviews Inc., United States (1991).
Carlier, V.A., et al., "Control of Asthma by in Vitro-Induced Allergen-Specific Regulatory T Cells in the Mouse," Munksgaard Allergy, 65:555, Jun. 2007).
Carlier, V.A., et al., "Increased Synapse Formation Obtained by T cell Epitopes Containing a CxxC Motif in Flanking Residues Convert CD4+ T Cells into Cytolytic Effectors," PLOS One, 7(10):e45366, Public Library of Science, United States (Oct. 2012).
Caro-Aguilar, I., et al., "Chimeric Epitopes Delivered by Polymeric Synthetic Linear Peptides Induce Protective Immunity to Malaria," Microbes and Infection, 7(13):1324-1337, Elsevier, France (Oct. 2005).
Castano, A.R., et al., "Peptide Binding and Presentation by Mouse CD1," Science, 269(5221):223-226, American Association for the Advancement of Science, United States (Jul. 1995).
Cavone, L., et al., "Long-Term Suppression of EAE Relapses by Pharmacological Impairment of Epitope Spreading," British Journal of Pharmacology, 171(6):1501-1509, Wiley, England (Mar. 2014).
Celis, E., et al., "Identification of Potential CTL Epitopes of Tumor-associated Antigen MAGE-1 for Five Common HLA-A Alleles," Molecular Immunology, 31(18):1423-1430, Pergamon Press, England (Dec. 1994).
Celis, E., et al., "Induction of Anti-Tumor Cytotoxic T Lymphocytes in Normal Humans Using Primary Cultures and Synthetic Peptide Epitopes," Proceedings of the National Academy of Sciences of the United States of America, 91(6):2105-2109, National Academy of Sciences, United States (Mar. 1994).
Chen, T.C., et al., "Induction of Dominant Transplantation Tolerance by an Altered Peptide Ligand of the Male Antigen Dby," The Journal of Clinical Investigation, 113(12):1754-1762, American Society for Clinical Investigation, United States (Jun. 2004).
Chen, X., et al., "Glucocorticoid Amplifies IL-2-Dependent Expansion of Functional FoxP3(+)CD4(+)CD25(+) T Regulatory Cells in Vivo and Enhances Their Capacity to Suppress EAE," European Journal of Immunology, 36(8):2139-2149, Wiley-VCH, Germany (Aug. 2006).
Chuanlin ed., Molecular Immunology, pp. 428-429, 433-436, 15 pages, Fudan University Press, Shanghai Medical College Press, (May 2001) (English Language Translation Provided).
Corthay, A., "CD4+ T Cells Cooperate With Macrophages for Specific Elimination of MHC Class II-Negative Cancer Cells," Advances in Experimental Medicine and Biology, 590:195-208, Kluwer Academic/Plenum Publishers, United States (2007).
Cotton, N.J., et al., "Oxidative Inhibition of Human Soluble Catechol-O-Methyltransferase," The Journal of Biological Chemistry, 279(22):23710-23718, American Society for Biochemistry and Molecular Biology, United States (May 2004).

Crellin, N.K., et al., "Altered Activation of AKT is Required for the Suppressive Function of Human CD4+CD25+ T Regulatory Cells," Blood, 109(5):2014-2022, American Society of Hematology, United States (Mar. 2007).
Crompton, P.D., et al., "Advances and Challenges in Malaria Vaccine Development," The Journal of Clinic Investigation, 120(12):4168-4178, American Society for Clinical Investigation, United States (Dec. 2010).
Davids, B.J., et al., "A New Family of Giardial Cysteine-rich Non-VSP Protein Genes and a Novel Cyst Protein," PLoS One, 1:e44, Public Library of Science, United States (Dec. 2006).
Davids, M.M., et al., "Interrogating the Repertoire: Broadening the Scope of Peptide-MHC Multimer Analysis," Nature Reviews. Immunology, 11(8):551-558, Nature Pub. Group, England (Jul. 2011).
De Groot, A.S. and Scott, D.W., "Immunogenicity of Protein Therapeutics," Trends in Immunology, 28(11):482-490, Elsevier Science Ltd., England (Nov. 2007).
De La Cruz, V.F., et al., "The Immunologic Significance of Variation Within Malaria Circumsporozoite Protein Sequences," Journal of Immunology, 142(10):3568-3575, American Association of Immunologists, United States (May 1989).
Desmetz, C., et al., "Proteomics-Based Identification of HSP60 as a Tumor-Associated Antigen in Early Stage Breast Cancer and Ductal Carcinoma in situ," Journal of Proteome Research, 7(9):3830-3837, American Chemical Society, United States (Sep. 2008).
Dobrzanski, M.J., "Expanding Roles for CD4 T Cells and Their Subpopulations in Tumor Immunity and Therapy," Frontiers in Oncology, 3:1-19, Frontiers Research Foundation, Switzerland (Mar. 2013).
Dobrzynski, E., et al., "Prevention of Cytotoxic T Lymphocyte Responses to Factor IX-Expressing Hepatocytes by Gene Transfer-induced Regulatory T Cells," Proceedings of the National Academy of Sciences of the United States of America, 103(12):4592-4597, National Academy of Sciences, United States (Mar. 2006).
Eberl, G., et al., "Tissue-specific Segregation of CD1d-dependent and CD1d-independent NK T Cells," Journal of Immunology, 162(11):6410-6419, American Association of Immunologists, United States (Jun. 1999).
Facktor, M.A., et al., "Hypersensitivity to Tetanus Toxoid," The Journal of Allergy and Clinical Immunology, 52(1):1-12, Mosby, United States (Jul. 1973).
Fan, C.F. and Mei, X.G., "Co-Immunization of BALB/c Mice With Recombinant Immunogens Containing G Protein Fragment and Chimeric CTL Epitope of Respiratory Syncytial Virus Induces Enhanced Cellular Immunity and High Level of Antibody Response," Vaccine, 23(35):4453-4461, Elsevier Science, Netherlands (Aug. 2005).
Fomenko, D.E. and Gladyshev, V.N., "Identity and Functions of Cxxc-derived Motifs," Biochemistry, 42(38):11214-11225, American Chemical Society, United States (Sep. 30, 2003).
Fournier, P. and Schirrrnacher, V., "Randomized Clinical Studies of Anti-tumor Vaccination: State of the Art in 2008," Expert Review of Vaccines, 8(1):51-66, Taylor & Francis, England (Jan. 2009).
Francois, V., et al., "The CD4(+) T-cell Response of Melanoma Patients to a MAGE-A3 Peptide Vaccine Involves Potential Regulatory T Cells," Cancer Research, 69(10):4335-4345, American Association for Cancer Research, United States (May 15, 2009).
Frankel, A.E., et al., "Characterization of Diphtheria Fusion Proteins Targeted to the Human Interleukin-3 Receptor," Protein Engineering, 13(8):575-581, Oxford University Press, England (Aug. 2000).
Ge, F.F., et al., "An Hsp70 Fusion Protein Vaccine Potentiates the Immune Response Against Japanese Encephalitis Virus," Archives of Virology, 152(1):125-135, Springer-Verlag, Austria (Jan. 2007).
Geluk, A., et al., "HLA-DR Binding Analysis of Peptides From Islet Antigens in IDDM," Diabetes, 47(10):1594-1601, American Diabetes Association, United States (Oct. 1998).
Gentile, F., et al., "Thyroglobulin as an Autoantigen: What Can We Learn About Immunopathogenicity From the Correlation of Antigenic Properties With Protein Structure?," Immunology, 112(1):13-25, Blackwell Scientific Publications, England (May 2004).
Girardi, E., et al., "Structure of an A-helical Peptide and Lipopeptide Bound to the Nonclassical Major Histocompatibility Complex (MHC)

(56) References Cited

OTHER PUBLICATIONS

Class I Molecule CD1d," The Journal of Biological Chemistry, 291(20):10677-10683, American Society for Biochemistry and Molecular Biology, United States (May 13, 2016).

Gross, D.A., et al., "Simple Conditioning With Monospecific CD4+ CD25+ Regulatory T Cells for Bone Marrow Engraftment and Tolerance to Multiple Gene Products," Blood, 108(6):1841-1848, American Society of Hematology, United States (Sep. 15, 2006).

Grossman, W.J., et al., "Differential Expression of Granzymes a and B in Human Cytotoxic Lymphocyte Subsets and T Regulatory Cells," Blood, 104(9):2840-2848, American Society of Hematology, United States (Nov. 2004).

Haga, J.A., et al., "HLA-A, Partial [Homo sapiens]," GenBank: AAA59610.1, 1995, p. 1.

Haque, M.A., et al., "Cysteinylation of Mhc Class Ii Ligands: Peptide Endocytosis and Reduction Within Apc Influences T Cell Recognition," Journal of Immunology (Baltimore, Md. : 1950), 166(7):4543-4551, American Association of Immunologists, United States (Apr. 1, 2001).

Harris, S.J., et al., "Prediction of Murine Mhc Class I Epitopes in a Major House Dust Mite Allergen and Induction of T1-type CD8+ T Cell Responses," International Immunology, 9(2):273-280, Oxford University Press, England (Feb. 1997).

Haveman, L.M. et al., "Induction and Capture of CD4+ Cytotoxic Adenoviral Specific T-Cells in Response to pan-DR Binding Adenoviral Epitopes; towards Immunotherapy," Blood, 106(11):3238, American Society of Hematology, United States (Nov. 2005).

Haveman, L.M., et al., "Novel Pan-DR-binding T Cell Epitopes of Adenovirus Induce Pro-inflammatory Cytokines and Chemokines in Healthy Donors," International Immunology, 18(11):1521-1529, Oxford University Press, 1989, England (Nov. 2006).

Heemskerk, B., et al., "Adenovirus-specific CD4+ T Cell Clones Recognizing Endogenous Antigen Inhibit Viral Replication in Vitro Through Cognate Interaction," Journal of Immunology (Baltimore, Md. : 1950), 177(12):8851-8859, American Association of Immunologists, United States (Dec. 15, 2006).

Hemmer, B., et al., "Minimal Peptide Length Requirements for CD4(+) T Cell Clones—implications for Molecular Mimicry and T Cell Survival," International Immunology, 12(3):375-383, Oxford University Press, 1989, England (Mar. 2000).

Heurtault, B., et al., "Design of a Liposomal Candidate Vaccine Against Pseudomonas Aeruginosa and its Evaluation in Triggering Systemic and Lung Mucosal Immunity," Pharmaceutical Research, 26(2):276-285, Kluwer Academic/Plenum Publishers, United States (Feb. 2009).

Ho, L.P., et al., "CD4(-)CD8alphaalpha Subset of CD1d-restricted NKT Cells Controls T Cell Expansion," Journal of Immunology (Baltimore, Md. : 1950), 172(12):7350-7358, American Association of Immunologists, United States (Jun. 2004).

Hohn, H., et al., "CD4+ Tumor-infiltrating Lymphocytes in Cervical Cancer Recognize HLA-DR-restricted Peptides Provided by Human Papillomavirus-E7," Journal of Immunology (Baltimore, Md. : 1950), 163(10):5715-5722, American Association of Immunologists, United States (Nov. 15, 1999).

Hori, S., et al., "Control of Regulatory T Cell Development by the Transcription Factor Foxp3," Science, 299(5609):1057-1061, American Association for the Advancement of Science, United States (Feb. 2003).

Hsu, H.J., et al., "Assessing Computational Amino Acid Beta-turn Propensities With a Phage-displayed Combinatorial Library and Directed Evolution," Structure (London, England : 1993), 14(10):1499-1510, Cambridge, Mass. : Cell Press, United States (Oct. 2006).

Hulo, N., et al., "The Prosite Database," Nucleic Acids Research 34(Database issue):D227-D230, Oxford University Press, England (Jan. 2006).

Iqbalsyah, T.M., et al., "The CXXC Motif at the N Terminus of an Alpha-helical Peptide," Protein Science : a Publication of the Protein Society, 15(8):1945-1950, Cold Spring Harbor Laboratory Press, United States (Aug. 2006).

Ise, W., et al., "Naive CD4+ T Cells Exhibit Distinct Expression Patterns of Cytokines and Cell Surface Molecules on Their Primary Responses to Varying Doses of Antigen," Journal of Immunology (Baltimore, Md. : 1950), 168(7):3242-3250, American Association of Immunologists (Apr. 2002).

James, E., et al., "HY Peptides Modulate Transplantation Responses to Skin Allografts," International Immunology, 14(11):1333-1342, Oxford University Press, 1989, England (Nov. 2002).

Janeway, C.A., et al., "Immunobiology, 3rd edition," Garland Press Inc., 1997, p. 11.

Janssens, W., et al., "CD4+CD25+ T Cells Lyse Antigen-presenting B Cells by Fas-fas Ligand Interaction in an Epitope-specific Manner," Journal of immunology (Baltimore, Md. : 1950), 171(9):4604-4612, American Association of Immunologists, United States (Nov. 2003).

Jensen, P.E., "Acidification and Disulfide Reduction Can be Sufficient to Allow Intact Proteins to Bind Class II MHC," Journal of Immunology, 150(8 Pt 1):3347-3356, American Association of Immunologists, United States (Apr. 1993).

Jiang, E.P., et al., "Protection by the Gross Saponins of Tribulus Terrestris Against Cerebral Ischemic Injury in Rats Involves the NF-KB Pathway," Acta Pharmaceutica Sinica B, 1(1):21-26, (Jun. 2011).

Joffre, O., et al., "Induction of Antigen-specific Tolerance to Bone Marrow Allografts With CD4+CD25+ T Lymphocytes," Blood, 103(11):4216-4221, American Society of Hematology, United States (Jun. 1, 2004).

Karin, N., et al., "Reversal of Experimental Autoimmune Encephalomyelitis by a Soluble Peptide Variant of a Myelin Basic Protein Epitope: T Cell Receptor Antagonism and Reduction of Interferon Gamma and Tumor Necrosis Factor Alpha Production," The Journal of Experimental Medicine, 180(6):2227-2237, Rockefeller University Press, United States (Dec. 1, 1994).

Kasprowicz, V., et al., "Tracking of Peptide-specific CD4+ T-cell Responses After an Acute Resolving Viral Infection: a Study of Parvovirus B19," Journal of Virology, 80(22):11209-11217, American Society For Microbiology, United States (Nov. 2006).

Khare, M., et al., "HLA Class Ii Transgenic Mice Authenticate Restriction of Myelin Oligodendrocyte Glycoprotein-specific Immune Response Implicated in Multiple Sclerosis Pathogenesis," International Immunology, 15(4):535-546, Oxford University Press, 1989, England (Apr. 2003).

Klebanoff, C.A., et al., "Therapeutic Cancer Vaccines: Are We There Yet?," Immunological reviews, 239(1):27-44, Blackwell, England (Jan. 2011).

Kumar, K.V.S.H., et al., "Twins and Endocrinology," Indian Journal of Endocrinology and Metabolism, 18(Suppl 1): S48-S52, Medknow Publications, India (Nov. 2014).

Laforge, M., et al., "HIV/SIV Infection Primes Monocytes and Dendritic Cells for Apoptosis," PLOS Pathogens 7(6):1-16, Public Library of Science, United States (Jun. 2011).

Lamb, J.R., et al., "Human T-Cell Clones Recognize Chemically Synthesized Peptides of Influenza Haemagglutinin," Nature, 300:66-69, Springer, United States (Nov. 1982).

Lewin, A., et al., "Effects of Substitutions in the CXXC Active-site Motif of the Extracytoplasmic Thioredoxin Resa," The Biochemical Journal, 414(1):81-91, Published by Portland Press on behalf of the Biochemical Society, England (Aug. 15, 2008).

Li, S.C., et al., "Twisting Immune Responses for Allogeneic Stem Cell Therapy," World Journal of Stem Cells, 1(1):30-35, Baishideng Publishing Group, United States (Dec. 31, 2009).

Lindqvist, C.A., et al., "Both CD4+ FoxP3+ and CD4+ FoxP3-T Cells From Patients With B-cell Malignancy Express Cytolytic Markers and Kill Autologous Leukaemic B Cells in Vitro," Immunology, 133(3):296-306, Blackwell Scientific Publications (Apr. 5, 2011).

Lodish, L., et al., "Molecular Cell Biology, 4th edition." W.H. Freeman & Co Ltd, New York, 2000, Section 6.3, Viruses: Structure, Function, and Uses, 1280 pages.

Louis, S., et al., "Contrasting CD25hiCD4+t Cells/foxp3 Patterns in Chronic Rejection and Operational Drug-free Tolerance," Transplantation, 81(3):398-407, Lippincott Williams & Wilkins (Feb. 15, 2006).

(56) References Cited

OTHER PUBLICATIONS

Lovitch, S.B., et al., "Amino-Terminal Flanking Residues Determine the Conformation of a Peptide-Class II MHC Complex," Journal of Immunology (Baltimore, Md. : 1950), 176(5):2958-2968, American Association of Immunologists, United States (Mar. 1, 2006).
Mach, B., et al., "Regulation of MHC Class II Genes: Lessons From a Disease," Annual Review of Immunology, 14:301-331, Annual Reviews Inc., c1983, United States (1996).
Maeda, M., et al., "CD1d-independent NKT Cells in Beta 2-microglobulin-deficient Mice Have Hybrid Phenotype and Function of Nk and T Cells," Journal of Immunology (Baltimore, Md. : 1950), 172(10):6115-6122, American Association of Immunologists, United States (May 15, 2004).
Maekawa, A., et al., "Evidence for a Domain-Swapped CD4 Dimer as the Coreceptor for Binding to Class II MHC," Journal of Immunology (Baltimore, Md. : 1950), 176(11):6873-6878, American Association of Immunologists (Jun. 1, 2006).
Markovicplese, S., et al., "T Cell Recognition of Immunodominant and Cryptic Proteolipid Protein Epitopes in Humans," Journal of Immunology (Baltimore, Md. : 1950), 155(2):982-992, American Association of Immunologists (Jul. 15, 1995).
Marti, M., et al., "Conformationally Correct Expression of Membrane-anchored Toxoplasma Gondii SAG1 in the Primitive Protozoan Giardia Duodenalis," Infection and Immunity, 70(2):1014-1016, American Society For Microbiology, United States (Feb. 2002).
Massilamany, C., et al., "Detection of Autoreactive CD4 T Cells Using Major Histocompatibility Complex Class II Dextramers," BMC Immunology, 12:40, BioMed Central, England (Jul. 2011).
Matsuda, J.L., et al., "CD1d-restricted INKT Cells, the 'Swiss-Army Knife' of the Immune System," Current Opinion in Immunology, 20(3):358-368, Elsevier, England (Jun. 2008).
Matthias, L.J., et al., "Disulfide Exchange in Domain 2 of CD4 is Required for Entry of HIV-1," Nature Immunology, 3(8):727-732, Nature America Inc. c2000, United States (Aug. 2002).
Maynard, C.L., et al., "Regulatory T Cells Expressing Interleukin 10 Develop From Foxp3+ and Foxp3-Precursor Cells in the Absence of Interleukin 10," Nature Immunology, 8(9):931-941, Nature America Inc. c2000, United States (Sep. 2007).
Merkler, D., et al., "Myelin Oligodendrocyte Glycoprotein-induced Experimental Autoimmune Encephalomyelitis in the Common Marmoset Reflects the Immunopathology of Pattern II Multiple Sclerosis Lesions," Multiple Sclerosis (Houndmills, Basingstoke, England), 12(4):369-374, SAGE Publications, England (Aug. 2006).
Moldovan, M.C., et al., "CD4 Dimers Constitute the Functional Component Required for T Cell Activation," Journal of Immunology (Baltimore, Md. : 1950), 169(11):6261-6268, American Association of Immunologists (Dec. 1, 2002).
Nepom, G.T., "MHC Class II Tetramers," The Journal of Immunology, 188(6):2477-2482, American Association of Immunologists, United States (Mar. 2012).
Nielsen, M., et al., "Quantitative Predictions of Peptide Binding to Any HLA-DR Molecule of Known Sequence: NetMHCIIpan," PLoS computational biology, 4(7):e1000107, Public Library of Science, [2005], United States (Jul. 4, 2008).
Ochoa-Garay, J., et al., "The Ability of Peptides to Induce Cytotoxic T Cells in Vitro Does Not Strongly Correlate With Their Affinity for the H-2ld Molecule: Implications for Vaccine Design and Immunotherapy," Molecular Immunology, 34(3):273-281, Pergamon Press, England (Feb. 1997).
Okubo, M., et al., "Analysis of HLA-DRB1 0901-Binding HPV-16 E7 Helper T Cell Epitope.," The Journal of Obstetrics and Gynaecology Research, 30(2):120-129, Wiley, Australia (Apr. 2004).
Oliveira, M.A., et al., "Insights into the Specificity of Thioredoxin Reductase-Thioredoxin Interactions. A Structural and Functional Investigation of the Yeast Thioredoxin System," Biochemistry, 49(15):3317-3326, American Chemical Society, United States (Apr. 2010).
O'Sullivan, D.M., et al., "MHC HLA-DR Gamma Chain, Partial [Homo sapiens]," GenBank AAA58655.1, 1994, p. 1.

Papanastasiou, P., et al., "Primary Structure and Biochemical Properties of a Varient-specific Surface Protein of Giardia.," Molecular and Biochemical Parasitology, 86(1):13-27, Elsevier/North-Holland Biomedical Press, Netherlands (May 1997).
Park, B., et al., "Redox Regulation Facilitates Optimal Peptide Selection by MHC Class I During Antigen Processing," Cell, 127(2):369-382, Cell Press, United States (Oct. 2006).
Parrino, J., et al., "Prevention of Immune Cell Apoptosis as Potential Therapeutic Strategy for Severe Infections," Emerging Infectious Diseases 13(2):191-198, National Center for Infectious Diseases, United States (Feb. 2007).
Peterson, R.A., "Regulatory T-cells: Diverse Phenotypes Integral to Immune Homeostasis and Suppression," Toxicologic Pathology, 40(2):186-204, Sage Publications, United States (2012).
Pillai, A.B., "Host NKT Cells Can Prevent Graft-versus-host Disease and Permit Graft Antitumor Activity After Bone Marrow Transplantation," Journal of Immunology , 178(10):6242-6251, American Association of Immunologists, United States (2007).
Pira, L.G., et al., "High Throughput T Epitope Mapping and Vaccine Development," Journal of Biomedicine & Biotechnology, 2010:12, Hindawi Pub. Corp, United States (Jun. 15, 2010).
Qin, W., et al., "Fusion Protein of CDR Mimetic Peptide With Fc Inhibit TNF-alpha Induced Cytotoxicity.," Molecular Immunology, 43(6):660-666, Pergamon Press, England (Feb. 2006).
Quintana, F, J., et al., "Epitope Spreading as an Early Pathogenic Event in Pediatric Multiple Sclerosis," Neurology, 83(24):2219-2226, Lippincott Williams & Wilkins, United States (Dec. 2014).
Racaniello, V., "How Many Viruses on Earth?," Virology Blog, 2013, 3 pages. Retrieved from Internet:[URL:http://www.virology.ws/2013/09/06/how-many-viruses-on-earth/].
Rammensee, H.G., et al., "MHC Ligands and Peptide Motifs," in Molecular Biology Intelligence Unit, p. 317, Springer, New York & Austin, Texas, USA (1997).
Reznik, S.I., et al., "Indirect Allorecognition of Mismatched Donor HLA Class Ii Peptides in Lung Transplant Recipients With Bronchiolitis Obliterans Syndrome," American Journal of Transplantation, 1(3):228-235, Wiley-Blackwell, United States (Sep. 2001).
Robinson, A.P., et al., "Vaccine Protocol," in Methods in Molecular Medicine, Humana Press, Totowa, NJ, Ed. Andrew Robinson, Michael J. Hudson and Martin P. Cranage, pp. 121-123 (2003).
Roep, B.O., et al., "The Problems and Promises of Research Into Human Immunology and Autoimmune Disease," Nature Medicine, 18(1):48-53, Nature Publishing Company, United States (Jan. 2012 ).
Roopenian, D., et al., "The Immunogenomics of Minor Histocompatibility Antigens.," Immunological Reviews, 190:86-94, Blackwell, England (Dec. 2002).
Roper, R.L., et al., "SARS Vaccines: Where Are We?," Expert Review of Vaccines, 8(7):887-898, Taylor & Francis, England (Jul. 2009).
Saez-Borderias, A., et al., "Expression and Function of NKG2D in CD4+ T cells Specific for Human Cytomegalovirus," European Journal of Immunology, 36(12):3198-3206, Wiley-VCH, Germany (Dec. 2006).
Santin, A, D, et al., "Human Papillomavirus Type 16 and 18 E7-Pulsed Dendritic Cell Vaccination of Stage IB or IIA Cervical Cancer Patients: A Phase I Escalating-Dose Trial," Journal of Virology, 82(4):1968-1979, American Society for Microbiology, United States (Feb. 2008).
Savoldo, B, et al., "Generation of EBV-specific CD4+ Cytotoxic T cells from Virus Naive Individuals," Journal of Immunology, 168(2):909-918, American Association of Immunologists, United States (Jan. 2002).
Schrieber, T.H., et al., "Tumor Immunogenicity and Responsiveness to Cancer Vaccine Therapy: the State of the Art," Seminars in Immunology, 22(3):105-112, Academic Press, Academic Press (Jun. 2010).
Schultz, E.S., et al., "A MAGE-A3 Peptide Presented by HLA-DP4 is Recognized on Tumor Cells by CD4+ Cytolytic T Lymphocyte," Cancer Research, 60(22):6272-6275, American Association for Cancer Research, United States (Nov. 2000).
Schwartz, R.H., et al., "The T Lymphocyte Response to Cytochrome c. V. Determination of the Minimal Peptide Size Required for

(56) References Cited

OTHER PUBLICATIONS

Stimulation of T Cell Clones and Assessment of the Contribution of Each Residue Beyond This Size to Antigenic Potency," Journal of Immunology, 135(4): 2598-2608, American Association of Immunologists, United States (Oct. 1985).
Sette, A and Fikes, J., "Epitope-based Vaccines: an Update on Epitope Identification, Vaccine Design and Delivery," Current Opinion in Immunology, 15(4):461-470, Elsevier, England (Aug. 2003).
Sette, A and Sidney, J., "HLA Supertypes and Supermotifs: a Functional Perspective on HLA Polymorphism," Current Opinion in Immunology, 10(4):478-482, Elsevier, England (Aug. 1998).
Shi, J and Bhattacharyya, M. K., "A Novel Plasma Membrane-bound Thioredoxin From Soybean," Plant Molecular Biology, 32(4): 653-662, Kluwer Academic, Netherlands (Nov. 1996).
Skonier, J., et al., "Human Transforming Growth Factor-beta Induced Gene Product (BIGH3) mRNA, Complete cds," GenBank M77349. 1, Jan. 14, 1995, 3 pages.
Stenstrom, M., et al., "Natural Killer T-cell Populations in C57BL/6 and NK1.1 Congenic BALB.NK Mice—a Novel Thymic Subset defined in BALB.NK Mice.," Immunology, 114(3):336-345, Blackwell Scientific Publications, England (Mar. 2005).
Straub, R. B., et al., "Allelic Variation in GAD1 (GAD67) is Associated With Schizophrenia and Influences Cortical Function and Gene Expression," Molecular Psychiatry, 12(9):854-869, Nature Publishing Group Specialist Journals, England (Sep. 2007).
Sundar, S.K and Menezes, J., "Generation of Epstein-bar Virus Antigen-specific Suppressor T Cells in Vitro," International Journal of Cancer, 35(3):351-357, Wiley-Liss, United States (Mar. 1985).
Taylor, A., et al., "T Regulatory Cells and Allergy," Microbes and Infection, 7(7-8):1049-1055, Elsevier, France (Jun. 2005).
Texier, C., et al., "On the Diversity and Heterogeneity of H-2(D)-restricted Determinants and T Cell Epitopes From the Major Bee Venom Allergen," International Immunology, 11(8):1313-1326, Oxford, England (Aug. 1999).
Thomson, S.A., et al., "Targeting a Polyepitope Protein Incorporating Multiple Class 11-restricted Viral Epitopes to the Secretory/endocytic Pathway Facilitates Immune Recognition by CD4+ Cytotoxic T Lymphocytes: a Novel Approach to Vaccine Design," Journal of Virology, 72(3):2246-2252, American Society For Microbiology, United States (Mar. 1998).
Tindle, R.W., et al., "A "Public" T-helper Epitope of the E7 Transforming Protein of Human Papillomavirus 16 Provides Cognate Help for Several E7 B-cell Epitopes From Cervical Cancer-associated Human Papillomavirus Genotypes," Proceedings of the National Academy of Sciences of the United States of America, 88(13):5887-5891, National Academy of Sciences, United States (Jul. 1991).
Tisch, R and McDevitt, H.O., "Antigen-specific Immunotherapy: is it a Real Possibility to Combat T-cell-mediated Autoimmunity?," Proceedings of the National Academy of Sciences of the United States of America, 91(2):437-438, National Academy of Sciences, United States (Jan. 1994).
Toyokawa, H., et al., "Relative Contribution of Direct and Indirect Allorecognition in Developing Tolerance After Liver Transplantation," Liver Transplantation, 14(3):346-357, Wiley, United States (Mar. 2008).
Tsuji, N.M., et al., "Antigen-specific, CD4+CD25+ Regulatory T Cell Clones Induced in Peyer's Patches," International Immunology, 15(4):525-534, Oxford, England (Apr. 2003).
Vignali, D.A. and Strominger, J.L., "Amino Acid Residues That Flank Core Peptide Epitopes and the Extracellular Domains of CD4 Modulate Differential Signaling Through the T Cell Receptor," The Journal of Experimental Medicine, 179(6):1945-1956, Rockefeller University Press, United States (Jun. 1994).
Voo, K.S., et al., "Functional Characterization of Ebv-encoded Nuclear Antigen 1-specific CD4+ Helper and Regulatory T Cells Elicited by in Vitro Peptide Stimulation," Cancer Research, 65(4):1577-1586, American Association for Cancer Research, United States (Feb. 2006).

Wang et al., "Generation and characterization of HLA-A 2.1 restricted and Prostein 31-39 specific NKT cell lines," Acta Academiae Medicine Militaris Tertiae, 28(16):1652-1655 (2006) (English language translation provided) (11 pages).
Wang, R.F., "Immune Suppression by Tumor-specific CD4+ Regulatory T-cells in Cancer," Seminars in Cancer Biology, 16(1):73-79, Academic Press, England (Feb. 2005).
Weissert, R., et al., "MHC Class Ii-regulated Central Nervous System Autoaggression and T Cell Responses in Peripheral Lymphoid Tissues are Dissociated in Myelin Oligodendrocyte Glycoprotein-induced Experimental Autoimmune Encephalomyelitis.," Journal of Immunology, 166(12):7588-7599, American Association of Immunologists, United States (Jun. 2001).
Wekerle, H., et al., "Autoimmunity's Next Top Models," Nature Medicine, 18(1):66-70, Nature Publishing Company, United States (Jan. 2012).
Wiker, H.G., et al., "Cloning, Expression and Significance of MPT53 for Identification of Secreted Proteins of Mycobacterium Tuberculosis," Microbial Pathogenesis, 26(4):207-219, Academic Press, England (Apr. 1999).
Witmer, C. and Young, G., "Factor VIII Inhibitors in Hemophilia a: Rationale and Latest Evidence," Therapeutic Advances in Hematology, 4(1):59-72, Sage, England (Feb. 2013).
Wobus, A.M and Boheler, K.R., "Embryonic Stem Cells: Prospects for Developmental Biology and Cell Therapy," Physiological Reviews, 85(2):635-678, American Physiological Society, United States (Apr. 2005).
Wood, K.J and Sakaguchi, S., "Regulatory T Cells in Transplantation Tolerance," Nature Reviews. Immunology, 3(3):199-210, Nature Pub. Group, England (Mar. 2003).
Wooldridge, L., et al., "Tricks With Tetramers: How to Get the Most From Multimeric Peptide-MHC," Immunology, 126(2):147-164, Blackwell Scientific Publications, England (Feb. 2009).
Wu, T.C., et al., "Engineering an Intracellular Pathway for Major Histocompatibility Complex Class II Presentation of Antigens," Proceedings of the National Academy of Sciences of the United States of America, 92(25):11671-11675, National Academy of Sciences, United States (Dec. 1995).
Zeng, Z., et al., "Crystal Structure of Mouse CD1: an MHC-like Fold With a Large Hydrophobic Binding Groove," Science, 277(5324):339-345, American Association for the Advancement of Science, United States (Jul. 1997).
Zhang, D., et al., "Preclinical Experimental Models of Drug Metabolism and Disposition in Drug Discovery and Development," Acta Pharmaceutica Sinica B, 2(6):549-561, (Dec. 2012).
Zhang, Y., et al., "A Mage-3 Peptide Presented by HLA-DR1 to CD4+ T Cells That Were Isolated From a Melanoma Patient Vaccinated With a Mage-3 Protein," Journal of Immunology, 171(1):219-225, American Association of Immunologists, United States (Jul. 2003).
Zhao, D.M., et al., "Activated CD4+CD25+ T Cells Selectively Kill B Lymphocytes," Blood, 107(10):3925-3932, American Society of Hematology, United States (May 2006).
Guddat, Luke W. et al., "Structural analysis of three His32 mutants of DsbA: Support for an electrostatic role of His32 in DsbA stability", Protein Science, 1997, pp. 1893-1900.
Guddat, Luke W. et al., "Crystal structures of reduced and oxidized DsbA: investigation of domain motion and thiolate stabilization", Structure, 1998, vol. 6, No. 6, pp. 757-767.
Lu, Xijie et al., "Conserved Residues Flanking the Thiol/Disulfide Centers of Protein Disulfide Isomerase Are Not Essential for Catalysis of Thiol/Disulfide Exchange", Biochemistry, vol. 31, No. 17, 1992, p. 4205-4210.
Terpe, 2003, Overview of tag protein fusions: from molecular fusions: from molecular and biochemical fundamentals to commercial systems, Appl. Microbiol. Biotechnol., 60: 523:533.
Cong et al., 2012, Site-Specific PEGylation at Histidine Tags, Bioconjugate Chemistry, 23(2):248-263.
Galdiero et al., 2010, The Presence of a Single N-Terminal Histidine Residue Enhances the Fusogenic Properties of a Membranotropic Peptide Derived from Herpes Simplex Virus Type 1 Glycoprotein H, The Journal of Biological Chemistry, 285(22):17123-17136.

(56) References Cited

OTHER PUBLICATIONS

Muller, S., et al., "Spliceosomal Peptide P140 for Immunotherapy of Systemic Lupus Erythematosus: Results of Early Phase II Clinical Trial," Arthritis & Rheumatism: Official Journal of the American College of Rheumatology, 2008, vol. 58, No. 12, pp. 3873-3883.
Anez, G., et al., "Passage of Dengue Virus Type 4 Vaccine Candidates in Fetal Rhesus Lung Cells Selects Heparin-Sensitive Variants That Result in Loss of Infectivity and Immunogenicity in Rhesus Macaques," Journal of Virology, 2009, vol. 83, No. 20, pp. 10384-10394.
Tanja Kortemme et al., "Electrostatic Interactions in the Active Site of the N-Terminal Thioredoxin-like Domain of Protein Disulfide Isomerase", *Biochemistry*, 1996, 35, pp. 14503-14511.
U.S. Appl. No. 17/923,108, 371(c) dated Nov. 3, 2022, Carlier, et al.
U.S. Appl. No. 17/923,117, 371(c) dated Nov. 3, 2022, Erak, et al.
U.S. Appl. No. 17/923,215, 371(c) dated Nov. 3, 2022, Carlier, et al.
U.S. Appl. No. 17/923,217, 371(c) dated Nov. 3, 2022, Erak, et al.

* cited by examiner

FIG. 1

SEQUENCE LISTING

<160> NUMBER OF SEQ ID NOS: 116

<210> SEQ ID NO 1
<211> LENGTH: 17
<212> TYPE: PRT
<213> ORGANISM: Artificial Sequence
<220> FEATURE:
<223> OTHER INFORMATION: synthetic peptide

<400> SEQUENCE: 1

His Cys Pro Tyr Cys Ser Arg Val Val His Leu Tyr Arg Asn Gly Lys
1               5                   10                  15

Asp

<210> SEQ ID NO 2
<211> LENGTH: 12
<212> TYPE: PRT
<213> ORGANISM: Artificial Sequence
<220> FEATURE:
<223> OTHER INFORMATION: synthetic peptide

<400> SEQUENCE: 2

Ser Arg Val Val His Leu Tyr Arg Asn Gly Lys Asp
1               5                   10

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Val Val His Leu Tyr Arg Asn Gly Lys
1               5

<210> SEQ ID NO 4
<211> LENGTH: 17
<212> TYPE: PRT
<213> ORGANISM: Artificial Sequence
<220> FEATURE:
<223> OTHER INFORMATION: synthetic peptide

<400> SEQUENCE: 4

Tyr Arg Pro Pro Phe Ser Arg Val Val His Leu Tyr Arg Asn Gly Lys
1               5                   10                  15
Asp

<210> SEQ ID NO 5
<211> LENGTH: 5
<212> TYPE: PRT
<213> ORGANISM: Artificial Sequence
<220> FEATURE:
<223> OTHER INFORMATION: synthetic peptide

<400> SEQUENCE: 5

Tyr Arg Pro Pro Phe
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic peptide

<400> SEQUENCE: 6

His Cys Pro Tyr Cys
1               5

<210> SEQ ID NO 7
<211> LENGTH: 16
<212> TYPE: PRT
<213> ORGANISM: Artificial Sequence
<220> FEATURE:
<223> OTHER INFORMATION: synthetic peptide

<400> SEQUENCE: 7

Cys Pro Tyr Cys Ser Arg Val Val His Leu Tyr Arg Asn Gly Lys Asp
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: synthetic peptide

<400> SEQUENCE: 8

His Cys Pro Tyr Cys Ser Arg Val Val His Leu Tyr Arg Asn Gly Lys
1               5                   10                  15

<210> SEQ ID NO 9
<211> LENGTH: 19
<212> TYPE: PRT
<213> ORGANISM: Artificial Sequence
<220> FEATURE:
<223> OTHER INFORMATION: synthetic peptide

<400> SEQUENCE: 9

Cys Gly Phe Ser Ser Asn Tyr Cys Gln Ile Tyr Pro Pro Asn Ala Asn
1               5                   10                  15

Lys Ile Arg

<210> SEQ ID NO 10
<211> LENGTH: 20
<212> TYPE: PRT
<213> ORGANISM: Artificial Sequence
<220> FEATURE:
<223> OTHER INFORMATION: synthetic peptide

<400> SEQUENCE: 10

His Cys Gly Phe Ser Ser Asn Tyr Cys Gln Ile Tyr Pro Pro Asn Ala
1               5                   10                  15

Asn Lys Ile Arg
            20

<210> SEQ ID NO 11
<211> LENGTH: 20
<212> TYPE: PRT
<213> ORGANISM: Artificial Sequence
<220> FEATURE:
<223> OTHER INFORMATION: synthetic peptide

<400> SEQUENCE: 11

His Cys Gly Phe Cys Ser Asn Tyr Cys Gln Ile Tyr Pro Pro Asn Ala
1               5                   10                  15

Asn Lys Ile Arg
            20

<210> SEQ ID NO 12
<211> LENGTH: 15
<212> TYPE: PRT
<213> ORGANISM: Artificial Sequence
<220> FEATURE:
<223> OTHER INFORMATION: synthetic peptide

<400> SEQUENCE: 12

Cys His Gly Ser Glu Pro Cys Ile Ile His Arg Gly Lys Pro Phe
1               5                   10                  15

<210> SEQ ID NO 13

```
<211> LENGTH: 16
<212> TYPE: PRT
<213> ORGANISM: Artificial Sequence
<220> FEATURE:
<223> OTHER INFORMATION: synthetic peptide

<400> SEQUENCE: 13

His Cys His Gly Ser Glu Pro Cys Ile Ile His Arg Gly Lys Pro Phe
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: synthetic peptide

<400> SEQUENCE: 14

His Cys His Gly Cys Glu Pro Cys Ile Ile His Arg Gly Lys Pro Phe
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (3)..(3)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 15

His Cys Xaa Gly Ser Glu Pro Cys Ile Ile His Arg Gly Lys Pro Phe
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (3)..(3)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 16

His Cys Xaa Gly Cys Glu Pro Cys Ile Ile His Arg Gly Lys Pro Phe
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: synthetic peptide

<400> SEQUENCE: 17

Cys His Gly Cys Ala Gln Lys Lys Ile Ile Ala Glu Lys
1               5                   10

<210> SEQ ID NO 18
<211> LENGTH: 14
<212> TYPE: PRT
<213> ORGANISM: Artificial Sequence
<220> FEATURE:
```

```
<223> OTHER INFORMATION: synthetic peptide

<400> SEQUENCE: 18

His Cys His Gly Cys Ala Gln Lys Lys Ile Ile Ala Glu Lys
1               5                   10

<210> SEQ ID NO 19
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 19

His Cys Xaa Gly Cys Ala Gln Lys Lys Ile Ile Ala Glu Lys
1               5                   10

<210> SEQ ID NO 20
<211> LENGTH: 13
<212> TYPE: PRT
<213> ORGANISM: Artificial Sequence
<220> FEATURE:
<223> OTHER INFORMATION: synthetic peptide

<400> SEQUENCE: 20

Cys Gly Pro Cys Met Asn Glu Glu Leu Thr Glu Arg Leu
1               5                   10

<210> SEQ ID NO 21
<211> LENGTH: 14
<212> TYPE: PRT
<213> ORGANISM: Artificial Sequence
<220> FEATURE:
<223> OTHER INFORMATION: synthetic peptide

<400> SEQUENCE: 21

His Cys Gly Pro Cys Met Asn Glu Glu Leu Thr Glu Arg Leu
1               5                   10

<210> SEQ ID NO 22
<211> LENGTH: 13
<212> TYPE: PRT
<213> ORGANISM: Artificial Sequence
<220> FEATURE:
<223> OTHER INFORMATION: synthetic peptide

<400> SEQUENCE: 22

Cys Gly Pro Ser Ala Ala Leu Thr Trp Val Gln Thr His
1               5                   10

<210> SEQ ID NO 23
<211> LENGTH: 14
<212> TYPE: PRT
<213> ORGANISM: Artificial Sequence
<220> FEATURE:
<223> OTHER INFORMATION: synthetic peptide

<400> SEQUENCE: 23

His Cys Gly Pro Ser Ala Ala Leu Thr Trp Val Gln Thr His
1               5                   10

<210> SEQ ID NO 24
<211> LENGTH: 14
```

```
<212> TYPE: PRT
<213> ORGANISM: Artificial Sequence
<220> FEATURE:
<223> OTHER INFORMATION: synthetic peptide

<400> SEQUENCE: 24

Cys His Gly Cys Pro Thr Leu Leu Tyr Val Leu Phe Glu Val
1               5                   10

<210> SEQ ID NO 25
<211> LENGTH: 15
<212> TYPE: PRT
<213> ORGANISM: Artificial Sequence
<220> FEATURE:
<223> OTHER INFORMATION: synthetic peptide

<400> SEQUENCE: 25

His Cys His Gly Cys Pro Thr Leu Leu Tyr Val Leu Phe Glu Val
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (3)..(3)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 26

His Cys Xaa Gly Cys Pro Thr Leu Leu Tyr Val Leu Phe Glu Val
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: synthetic peptide

<400> SEQUENCE: 27

Cys Gly Pro Cys Gly Gly Tyr Val Pro Phe His Ile Gln Val Pro
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: synthetic peptide

<400> SEQUENCE: 28

His Cys Gly Pro Cys Gly Gly Tyr Val Pro Phe His Ile Gln Val Pro
1               5                   10                  15

<210> SEQ ID NO 29
<211> LENGTH: 13
<212> TYPE: PRT
<213> ORGANISM: Artificial Sequence
<220> FEATURE:
<223> OTHER INFORMATION: synthetic peptide

<400> SEQUENCE: 29

Cys Gly His Cys Asp Lys His Ile Glu Gln Tyr Leu Lys
1               5                   10
```

```
<210> SEQ ID NO 30
<211> LENGTH: 14
<212> TYPE: PRT
<213> ORGANISM: Artificial Sequence
<220> FEATURE:
<223> OTHER INFORMATION: synthetic peptide

<400> SEQUENCE: 30

His Cys Gly His Cys Asp Lys His Ile Glu Gln Tyr Leu Lys
1               5                   10

<210> SEQ ID NO 31
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (4)..(4)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 31

His Cys Gly Xaa Cys Asp Lys His Ile Glu Gln Tyr Leu Lys
1               5                   10

<210> SEQ ID NO 32
<211> LENGTH: 13
<212> TYPE: PRT
<213> ORGANISM: Artificial Sequence
<220> FEATURE:
<223> OTHER INFORMATION: synthetic peptide

<400> SEQUENCE: 32

Cys Gly His Cys Glu Lys Lys Ile Cys Lys Met Glu Lys
1               5                   10

<210> SEQ ID NO 33
<211> LENGTH: 14
<212> TYPE: PRT
<213> ORGANISM: Artificial Sequence
<220> FEATURE:
<223> OTHER INFORMATION: synthetic peptide

<400> SEQUENCE: 33

His Cys Gly His Cys Glu Lys Lys Ile Cys Lys Met Glu Lys
1               5                   10

<210> SEQ ID NO 34
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (4)..(4)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 34

His Cys Gly Xaa Cys Glu Lys Lys Ile Cys Lys Met Glu Lys
1               5                   10

<210> SEQ ID NO 35
<211> LENGTH: 13
```

```
<212> TYPE: PRT
<213> ORGANISM: Artificial Sequence
<220> FEATURE:
<223> OTHER INFORMATION: synthetic peptide

<400> SEQUENCE: 35

Cys Gly His Cys Lys Tyr Val Lys Gln Asn Thr Leu Lys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: synthetic peptide

<400> SEQUENCE: 36

His Cys Gly His Cys Lys Tyr Val Lys Gln Asn Thr Leu Lys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (4)..(4)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 37

His Cys Gly Xaa Cys Lys Tyr Val Lys Gln Asn Thr Leu Lys
1               5                   10

<210> SEQ ID NO 38
<211> LENGTH: 13
<212> TYPE: PRT
<213> ORGANISM: Artificial Sequence
<220> FEATURE:
<223> OTHER INFORMATION: synthetic peptide

<400> SEQUENCE: 38

Cys Gly His Cys Glu His Pro Ile Val Val Ser Gly Ser
1               5                   10

<210> SEQ ID NO 39
<211> LENGTH: 14
<212> TYPE: PRT
<213> ORGANISM: Artificial Sequence
<220> FEATURE:
<223> OTHER INFORMATION: synthetic peptide

<400> SEQUENCE: 39

His Cys Gly His Cys Glu His Pro Ile Val Val Ser Gly Ser
1               5                   10

<210> SEQ ID NO 40
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (4)..(4)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val
```

<400> SEQUENCE: 40

His Cys Gly Xaa Cys Glu His Pro Ile Val Val Ser Gly Ser
1               5                   10

<210> SEQ ID NO 41
<211> LENGTH: 13
<212> TYPE: PRT
<213> ORGANISM: Artificial Sequence
<220> FEATURE:
<223> OTHER INFORMATION: synthetic peptide

<400> SEQUENCE: 41

Cys Gly His Cys Arg Ala Met Tyr Ala Pro Pro Ile Ala
1               5                   10

<210> SEQ ID NO 42
<211> LENGTH: 14
<212> TYPE: PRT
<213> ORGANISM: Artificial Sequence
<220> FEATURE:
<223> OTHER INFORMATION: synthetic peptide

<400> SEQUENCE: 42

His Cys Gly His Cys Arg Ala Met Tyr Ala Pro Pro Ile Ala
1               5                   10

<210> SEQ ID NO 43
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (4)..(4)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 43

His Cys Gly Xaa Cys Arg Ala Met Tyr Ala Pro Pro Ile Ala
1               5                   10

<210> SEQ ID NO 44
<211> LENGTH: 14
<212> TYPE: PRT
<213> ORGANISM: Artificial Sequence
<220> FEATURE:
<223> OTHER INFORMATION: synthetic peptide

<400> SEQUENCE: 44

Cys His Gly Cys Tyr Cys Ala Val Pro Asp Asp Pro Asp Ala
1               5                   10

<210> SEQ ID NO 45
<211> LENGTH: 15
<212> TYPE: PRT
<213> ORGANISM: Artificial Sequence
<220> FEATURE:
<223> OTHER INFORMATION: synthetic peptide

<400> SEQUENCE: 45

His Cys His Gly Cys Tyr Cys Ala Val Pro Asp Asp Pro Asp Ala
1               5                   10                  15

<210> SEQ ID NO 46
<211> LENGTH: 15

```
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: VARIANT
<222> LOCATION: (3)..(3)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 46

His Cys Xaa Gly Cys Tyr Cys Ala Val Pro Asp Asp Pro Asp Ala
1               5                   10                  15

<210> SEQ ID NO 47
<211> LENGTH: 17
<212> TYPE: PRT
<213> ORGANISM: Artificial Sequence
<220> FEATURE:
<223> OTHER INFORMATION: synthetic peptide

<400> SEQUENCE: 47

Cys Gly His Cys Gly Gly Ile Arg Leu His Pro Thr His Tyr Ser Ile
1               5                   10                  15

Arg

<210> SEQ ID NO 48
<211> LENGTH: 18
<212> TYPE: PRT
<213> ORGANISM: Artificial Sequence
<220> FEATURE:
<223> OTHER INFORMATION: synthetic peptide

<400> SEQUENCE: 48

His Cys Gly His Cys Gly Gly Ile Arg Leu His Pro Thr His Tyr Ser
1               5                   10                  15

Ile Arg

<210> SEQ ID NO 49
<211> LENGTH: 18
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (4)..(4)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 49

His Cys Gly Xaa Cys Gly Gly Ile Arg Leu His Pro Thr His Tyr Ser
1               5                   10                  15

Ile Arg

<210> SEQ ID NO 50
<211> LENGTH: 13
<212> TYPE: PRT
<213> ORGANISM: Artificial Sequence
<220> FEATURE:
<223> OTHER INFORMATION: synthetic peptide

<400> SEQUENCE: 50
```

Cys His Gly Cys Tyr Arg Gln Val Pro Gly Ser Asp Pro
1               5                   10

<210> SEQ ID NO 51
<211> LENGTH: 14
<212> TYPE: PRT
<213> ORGANISM: Artificial Sequence
<220> FEATURE:
<223> OTHER INFORMATION: synthetic peptide

<400> SEQUENCE: 51

His Cys His Gly Cys Tyr Arg Gln Val Pro Gly Ser Asp Pro
1               5                   10

<210> SEQ ID NO 52
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: VARIANT
<222> LOCATION: (3)..(3)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 52

His Cys Xaa Gly Cys Tyr Arg Gln Val Pro Gly Ser Asp Pro
1               5                   10

<210> SEQ ID NO 53
<211> LENGTH: 13
<212> TYPE: PRT
<213> ORGANISM: Artificial Sequence
<220> FEATURE:
<223> OTHER INFORMATION: synthetic peptide

<400> SEQUENCE: 53

Cys His Gly Cys Phe Val Ala Leu Cys Ala Thr Asp Val
1               5                   10

<210> SEQ ID NO 54
<211> LENGTH: 14
<212> TYPE: PRT
<213> ORGANISM: Artificial Sequence
<220> FEATURE:
<223> OTHER INFORMATION: synthetic peptide

<400> SEQUENCE: 54

His Cys His Gly Cys Phe Val Ala Leu Cys Ala Thr Asp Val
1               5                   10

<210> SEQ ID NO 55
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 55

```
His Cys Xaa Gly Cys Phe Val Ala Leu Cys Ala Thr Asp Val
1               5                   10
```

<210> SEQ ID NO 56
<211> LENGTH: 13
<212> TYPE: PRT
<213> ORGANISM: Artificial Sequence
<220> FEATURE:
<223> OTHER INFORMATION: synthetic peptide

<400> SEQUENCE: 56

```
Cys His Gly Cys Phe Lys Glu Leu Glu Gly Trp Glu Pro
1               5                   10
```

<210> SEQ ID NO 57
<211> LENGTH: 14
<212> TYPE: PRT
<213> ORGANISM: Artificial Sequence
<220> FEATURE:
<223> OTHER INFORMATION: synthetic peptide

<400> SEQUENCE: 57

```
His Cys His Gly Cys Phe Lys Glu Leu Glu Gly Trp Glu Pro
1               5                   10
```

<210> SEQ ID NO 58
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 58

```
His Cys Xaa Gly Cys Phe Lys Glu Leu Glu Gly Trp Glu Pro
1               5                   10
```

<210> SEQ ID NO 59
<211> LENGTH: 13
<212> TYPE: PRT
<213> ORGANISM: Artificial Sequence
<220> FEATURE:
<223> OTHER INFORMATION: synthetic peptide

<400> SEQUENCE: 59

```
Cys His Gly Cys Val Ala Ser Ser Tyr Ala Ala Ala Gln
1               5                   10
```

<210> SEQ ID NO 60
<211> LENGTH: 14
<212> TYPE: PRT
<213> ORGANISM: Artificial Sequence
<220> FEATURE:
<223> OTHER INFORMATION: synthetic peptide

<400> SEQUENCE: 60

```
His Cys His Gly Cys Val Ala Ser Ser Tyr Ala Ala Ala Gln
1               5                   10
```

<210> SEQ ID NO 61
<211> LENGTH: 14
<212> TYPE: PRT
<213> ORGANISM: Artificial Sequence
<220> FEATURE:

```
<223> OTHER INFORMATION: synthetic peptide
<220> FEATURE:
<221> NAME/KEY: misc_feature
<222> LOCATION: (3)..(3)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 61

His Cys Xaa Gly Cys Val Ala Ser Ser Tyr Ala Ala Ala Gln
1               5                   10

<210> SEQ ID NO 62
<211> LENGTH: 13
<212> TYPE: PRT
<213> ORGANISM: Artificial Sequence
<220> FEATURE:
<223> OTHER INFORMATION: synthetic peptide

<400> SEQUENCE: 62

Cys His Gly Cys Phe Asn Ser Asn Arg Ala Asn Ser Ser
1               5                   10

<210> SEQ ID NO 63
<211> LENGTH: 14
<212> TYPE: PRT
<213> ORGANISM: Artificial Sequence
<220> FEATURE:
<223> OTHER INFORMATION: synthetic peptide

<400> SEQUENCE: 63

His Cys His Gly Cys Phe Asn Ser Asn Arg Ala Asn Ser Ser
1               5                   10

<210> SEQ ID NO 64
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 64

His Cys Xaa Gly Cys Phe Asn Ser Asn Arg Ala Asn Ser Ser
1               5                   10

<210> SEQ ID NO 65
<211> LENGTH: 13
<212> TYPE: PRT
<213> ORGANISM: Artificial Sequence
<220> FEATURE:
<223> OTHER INFORMATION: synthetic peptide

<400> SEQUENCE: 65

Cys Gly His Cys Leu Val Leu Ala Pro Thr Arg Glu Leu
1               5                   10

<210> SEQ ID NO 66
<211> LENGTH: 14
<212> TYPE: PRT
<213> ORGANISM: Artificial Sequence
<220> FEATURE:
<223> OTHER INFORMATION: synthetic peptide

<400> SEQUENCE: 66
```

```
His Cys Gly His Cys Leu Val Leu Ala Pro Thr Arg Glu Leu
1               5                   10

<210> SEQ ID NO 67
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (4)..(4)
<223> OTHER INFORMATION: Xaa is Ala, Arg, Asn, Asp, Glu, Gln, Gly, Ile,
      Leu, Lys, Met, Phe, Pro, Ser, Thr, Trp, Tyr, or Val

<400> SEQUENCE: 67

His Cys Gly Xaa Cys Leu Val Leu Ala Pro Thr Arg Glu Leu
1               5                   10

<210> SEQ ID NO 68
<211> LENGTH: 13
<212> TYPE: PRT
<213> ORGANISM: Artificial Sequence
<220> FEATURE:
<223> OTHER INFORMATION: synthetic peptide

<400> SEQUENCE: 68

Cys Gly His Cys Pro Glu Phe Leu Glu Gln Lys Arg Ala
1               5                   10

<210> SEQ ID NO 69
<211> LENGTH: 14
<212> TYPE: PRT
<213> ORGANISM: Artificial Sequence
<220> FEATURE:
<223> OTHER INFORMATION: synthetic peptide

<400> SEQUENCE: 69

His Cys Gly His Cys Pro Glu Phe Leu Glu Gln Lys Arg Ala
1               5                   10

<210> SEQ ID NO 70
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 70

His Cys Gly Xaa Cys Pro Glu Phe Leu Glu Gln Lys Arg Ala
1               5                   10

<210> SEQ ID NO 71
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: VARIANT
<222> LOCATION: (2)..(3)
<223> OTHER INFORMATION: xaa can  be any amino acid

<400> SEQUENCE: 71

Cys Xaa Xaa Cys
```

```
<210> SEQ ID NO 72
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: VARIANT
<222> LOCATION: (2)..(3)
<223> OTHER INFORMATION: Xaa can be any amino acid

<400> SEQUENCE: 72

Cys Xaa Xaa Ser
1

<210> SEQ ID NO 73
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: VARIANT
<222> LOCATION: (2)..(3)
<223> OTHER INFORMATION: Xaa can be any amino acid

<400> SEQUENCE: 73

Cys Xaa Xaa Thr
1

<210> SEQ ID NO 74
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: VARIANT
<222> LOCATION: (2)..(3)
<223> OTHER INFORMATION: Xaa can be any amino acid

<400> SEQUENCE: 74

Ser Xaa Xaa Cys
1

<210> SEQ ID NO 75
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: VARIANT
<222> LOCATION: (2)..(3)
<223> OTHER INFORMATION: Xaa can be any amin acid

<400> SEQUENCE: 75

Thr Xaa Xaa Cys
1

<210> SEQ ID NO 76
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: VARIANT
```

```
<222> LOCATION: (1)..(1)
<223> OTHER INFORMATION: Xaa can be Cys, Ser or Thr
<220> FEATURE:
<221> NAME/KEY: VARIANT
<222> LOCATION: (2)..(3)
<223> OTHER INFORMATION: Xaa can be any amino acid

<400> SEQUENCE: 76

Xaa Xaa Xaa Cys
1

<210> SEQ ID NO 77
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: VARIANT
<222> LOCATION: (2)..(3)
<223> OTHER INFORMATION: Xaa can be any amino acid
<220> FEATURE:
<221> NAME/KEY: VARIANT
<222> LOCATION: (4)..(4)
<223> OTHER INFORMATION: Xaa can be Cys, Ser or Thr

<400> SEQUENCE: 77

Cys Xaa Xaa Xaa
1

<210> SEQ ID NO 78
<211> LENGTH: 5
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
<222> LOCATION: (3)..(4)
<223> OTHER INFORMATION: Xaa can be any amino acid
<220> FEATURE:
<221> NAME/KEY: VARIANT
<222> LOCATION: (5)..(5)
<223> OTHER INFORMATION: Xaa can be Cys, Ser or Thr

<400> SEQUENCE: 78

His Cys Xaa Xaa Xaa
1               5

<210> SEQ ID NO 79
<211> LENGTH: 5
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
<222> LOCATION: (1)..(1)
<223> OTHER INFORMATION: Xaa can be Cys, Ser or Thr
<220> FEATURE:
<221> NAME/KEY: VARIANT
<222> LOCATION: (2)..(3)
<223> OTHER INFORMATION: Xaa can be any amino acid

<400> SEQUENCE: 79

Xaa Xaa Xaa Cys His
1               5

<210> SEQ ID NO 80
<211> LENGTH: 5
<212> TYPE: PRT
```

```
<213> ORGANISM: Artificial Sequence
<220> FEATURE:
<223> OTHER INFORMATION: modified redox motif
<220> FEATURE:
<221> NAME/KEY: VARIANT
<222> LOCATION: (3)..(4)
<223> OTHER INFORMATION: Xaa can be any amino acid

<400> SEQUENCE: 80

His Cys Xaa Xaa Cys
1               5

<210> SEQ ID NO 81
<211> LENGTH: 5
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
<222> LOCATION: (3)..(4)
<223> OTHER INFORMATION: Xaa can be any amino acid

<400> SEQUENCE: 81

His Cys Xaa Xaa Ser
1               5

<210> SEQ ID NO 82
<211> LENGTH: 5
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
<222> LOCATION: (3)..(4)
<223> OTHER INFORMATION: Xaa can be any amino acid

<400> SEQUENCE: 82

His Cys Xaa Xaa Thr
1               5

<210> SEQ ID NO 83
<211> LENGTH: 5
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
<222> LOCATION: (2)..(3)
<223> OTHER INFORMATION: Xaa can be any amino acid

<400> SEQUENCE: 83

Cys Xaa Xaa Cys His
1               5

<210> SEQ ID NO 84
<211> LENGTH: 5
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
<222> LOCATION: (2)..(3)
<223> OTHER INFORMATION: Xaa can be any amino acid

<400> SEQUENCE: 84

Ser Xaa Xaa Cys His
```

```
1               5

<210> SEQ ID NO 85
<211> LENGTH: 5
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
<222> LOCATION: (2)..(3)
<223> OTHER INFORMATION: Xaa can be any amino acid

<400> SEQUENCE: 85

Thr Xaa Xaa Cys His
1               5

<210> SEQ ID NO 86
<211> LENGTH: 6
<212> TYPE: PRT
<213> ORGANISM: Artificial Sequence
<220> FEATURE:
<223> OTHER INFORMATION: Modified redox motif
<220> FEATURE:
<221> NAME/KEY: VARIANT
<222> LOCATION: (3)..(4)
<223> OTHER INFORMATION: Xaa can be any amino acid

<400> SEQUENCE: 86

His Cys Xaa Xaa Cys His
1               5

<210> SEQ ID NO 87
<211> LENGTH: 6
<212> TYPE: PRT
<213> ORGANISM: Artificial Sequence
<220> FEATURE:
<223> OTHER INFORMATION: late endosome targeting sequence
<220> FEATURE:
<221> NAME/KEY: VARIANT
<222> LOCATION: (1)..(1)
<223> OTHER INFORMATION: Xaa can be Asp or Glu
<220> FEATURE:
<221> NAME/KEY: VARIANT
<222> LOCATION: (2)..(4)
<223> OTHER INFORMATION: Xaa can be any amino acid
<220> FEATURE:
<221> NAME/KEY: VARIANT
<222> LOCATION: (6)..(6)
<223> OTHER INFORMATION: Xaa can be Ile or Leu

<400> SEQUENCE: 87

Xaa Xaa Xaa Xaa Leu Xaa
1               5

<210> SEQ ID NO 88
<211> LENGTH: 5
<212> TYPE: PRT
<213> ORGANISM: Artificial Sequence
<220> FEATURE:
<223> OTHER INFORMATION: late endosome targeting sequence
<220> FEATURE:
<221> NAME/KEY: VARIANT
<222> LOCATION: (2)..(3)
<223> OTHER INFORMATION: Xaa can be any amino acid

<400> SEQUENCE: 88

Asp Xaa Xaa Leu Leu
1               5
```

```
<210> SEQ ID NO 89
<211> LENGTH: 4
<212> TYPE: PRT
<213> ORGANISM: Artificial Sequence
<220> FEATURE:
<223> OTHER INFORMATION: late endosome targeting motif
<220> FEATURE:
<221> NAME/KEY: VARIANT
<222> LOCATION: (2)..(3)
<223> OTHER INFORMATION: Xaa can be any amino acid
<220> FEATURE:
<221> NAME/KEY: VARIANT
<222> LOCATION: (4)..(4)
<223> OTHER INFORMATION: Xaa can be Phe, Tyr or Trp

<400> SEQUENCE: 89

Tyr Xaa Xaa Xaa
1

<210> SEQ ID NO 90
<211> LENGTH: 6
<212> TYPE: PRT
<213> ORGANISM: Artificial Sequence
<220> FEATURE:
<223> OTHER INFORMATION: modfied redox motif
<220> FEATURE:
<221> NAME/KEY: VARIANT
<222> LOCATION: (2)..(2)
<223> OTHER INFORMATION: Xaa can be any amino acid
<220> FEATURE:
<221> NAME/KEY: VARIANT
<222> LOCATION: (4)..(5)
<223> OTHER INFORMATION: Xaa can be any amino acid
<220> FEATURE:
<221> NAME/KEY: VARIANT
<222> LOCATION: (6)..(6)
<223> OTHER INFORMATION: Xaa can be Cys, Ser or Thr

<400> SEQUENCE: 90

His Xaa Cys Xaa Xaa Xaa
1               5

<210> SEQ ID NO 91
<211> LENGTH: 7
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
<222> LOCATION: (2)..(3)
<223> OTHER INFORMATION: Xaa can be any amino acid
<220> FEATURE:
<221> NAME/KEY: VARIANT
<222> LOCATION: (5)..(6)
<223> OTHER INFORMATION: Xaa can be any amino acid
<220> FEATURE:
<221> NAME/KEY: VARIANT
<222> LOCATION: (7)..(7)
<223> OTHER INFORMATION: Xaa can be Cys, Ser or Thr

<400> SEQUENCE: 91

His Xaa Xaa Cys Xaa Xaa Xaa
1               5

<210> SEQ ID NO 92
<211> LENGTH: 6
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
```

```
<222> LOCATION: (1)..(1)
<223> OTHER INFORMATION: Xaa can be Cys, Ser or Thr
<220> FEATURE:
<221> NAME/KEY: VARIANT
<222> LOCATION: (2)..(3)
<223> OTHER INFORMATION: Xaa can be any amino acids
<220> FEATURE:
<221> NAME/KEY: VARIANT
<222> LOCATION: (5)..(5)
<223> OTHER INFORMATION: Xaa can be any amino acids

<400> SEQUENCE: 92

Xaa Xaa Xaa Cys Xaa His
1               5

<210> SEQ ID NO 93
<211> LENGTH: 7
<212> TYPE: PRT
<213> ORGANISM: Artificial Sequence
<220> FEATURE:
<223> OTHER INFORMATION: Modified redox motif
<220> FEATURE:
<221> NAME/KEY: VARIANT
<222> LOCATION: (1)..(1)
<223> OTHER INFORMATION: Xaa can be Cys, Ser or Thre
<220> FEATURE:
<221> NAME/KEY: VARIANT
<222> LOCATION: (2)..(3)
<223> OTHER INFORMATION: Xaa can be any amino acid
<220> FEATURE:
<221> NAME/KEY: VARIANT
<222> LOCATION: (5)..(6)
<223> OTHER INFORMATION: Xaa can be any amino acid

<400> SEQUENCE: 93

Xaa Xaa Xaa Cys Xaa Xaa His
1               5

<210> SEQ ID NO 94
<211> LENGTH: 6
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
<222> LOCATION: (2)..(3)
<223> OTHER INFORMATION: Xaa can be any amino acid
<220> FEATURE:
<221> NAME/KEY: VARIANT
<222> LOCATION: (5)..(5)
<223> OTHER INFORMATION: Xaa can be any amino acid

<400> SEQUENCE: 94

Cys Xaa Xaa Cys Xaa His
1               5

<210> SEQ ID NO 95
<211> LENGTH: 7
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
<222> LOCATION: (2)..(3)
<223> OTHER INFORMATION: Xaa can be any amino acid
<220> FEATURE:
<221> NAME/KEY: VARIANT
<222> LOCATION: (5)..(6)
<223> OTHER INFORMATION: Xaa can be any amino acid

<400> SEQUENCE: 95
```

```
Cys Xaa Xaa Cys Xaa Xaa His
1               5

<210> SEQ ID NO 96
<211> LENGTH: 6
<212> TYPE: PRT
<213> ORGANISM: Artificial Sequence
<220> FEATURE:
<223> OTHER INFORMATION: modified redox motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: VARIANT
<222> LOCATION: (4)..(5)
<223> OTHER INFORMATION: Xaa can be any amino acid

<400> SEQUENCE: 96

His Xaa Cys Xaa Xaa Cys
1               5

<210> SEQ ID NO 97
<211> LENGTH: 7
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
<222> LOCATION: (2)..(3)
<223> OTHER INFORMATION: Xaa can be any amino acid
<220> FEATURE:
<221> NAME/KEY: VARIANT
<222> LOCATION: (5)..(6)
<223> OTHER INFORMATION: Xaa can be any amino acid

<400> SEQUENCE: 97

His Xaa Xaa Cys Xaa Xaa Cys
1               5

<210> SEQ ID NO 98
<211> LENGTH: 6
<212> TYPE: PRT
<213> ORGANISM: Artificial Sequence
<220> FEATURE:
<223> OTHER INFORMATION: modified redox motif
<220> FEATURE:
<221> NAME/KEY: VARIANT
<222> LOCATION: (2)..(2)
<223> OTHER INFORMATION: Xaa can be any amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 98

His Xaa Cys Xaa Xaa Ser
1               5

<210> SEQ ID NO 99
<211> LENGTH: 7
<212> TYPE: PRT
<213> ORGANISM: Artificial Sequence
<220> FEATURE:
<223> OTHER INFORMATION: modified redox motif
<220> FEATURE:
<221> NAME/KEY: misc_feature
<222> LOCATION: (2)..(3)
<223> OTHER INFORMATION: Xaa can be any naturally occurring amino acid
<220> FEATURE:
```

```
<221> NAME/KEY: misc_feature
<222> LOCATION: (5)..(6)
<223> OTHER INFORMATION: Xaa can be any naturally occurring amino acid

<400> SEQUENCE: 99

His Xaa Xaa Cys Xaa Xaa Ser
1               5

<210> SEQ ID NO 100
<211> LENGTH: 6
<212> TYPE: PRT
<213> ORGANISM: Artificial Sequence
<220> FEATURE:
<223> OTHER INFORMATION: modified redox motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 100

His Xaa Xaa Cys Xaa Thr
1               5

<210> SEQ ID NO 101
<211> LENGTH: 7
<212> TYPE: PRT
<213> ORGANISM: Artificial Sequence
<220> FEATURE:
<223> OTHER INFORMATION: modified redox motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 101

His Xaa Xaa Cys Xaa Xaa Thr
1               5

<210> SEQ ID NO 102
<211> LENGTH: 6
<212> TYPE: PRT
<213> ORGANISM: Artificial Sequence
<220> FEATURE:
<223> OTHER INFORMATION: modified redox motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 102

Ser Xaa Xaa Cys Xaa His
1               5

<210> SEQ ID NO 103
<211> LENGTH: 7
<212> TYPE: PRT
<213> ORGANISM: Artificial Sequence
<220> FEATURE:
<223> OTHER INFORMATION: modified redox motif
```

```
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 103

Ser Xaa Xaa Cys Xaa Xaa His
1               5

<210> SEQ ID NO 104
<211> LENGTH: 6
<212> TYPE: PRT
<213> ORGANISM: Artificial Sequence
<220> FEATURE:
<223> OTHER INFORMATION: modified redox  motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 104

Thr Xaa Xaa Cys Xaa His
1               5

<210> SEQ ID NO 105
<211> LENGTH: 7
<212> TYPE: PRT
<213> ORGANISM: Artificial Sequence
<220> FEATURE:
<223> OTHER INFORMATION: Modified redox motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 105

Thr Xaa Xaa Cys Xaa Xaa His
1               5

<210> SEQ ID NO 106
<211> LENGTH: 5
<212> TYPE: PRT
<213> ORGANISM: Artificial Sequence
<220> FEATURE:
<223> OTHER INFORMATION: modified redox motif
<220> FEATURE:
<221> NAME/KEY: misc_feature
<222> LOCATION: (4)..(4)
<223> OTHER INFORMATION: Xaa can be any naturally occurring amino acid

<400> SEQUENCE: 106

His Cys His Xaa Cys
1               5

<210> SEQ ID NO 107
<211> LENGTH: 6
<212> TYPE: PRT
<213> ORGANISM: Artificial Sequence
<220> FEATURE:
```

<223> OTHER INFORMATION: modified redox motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 107

Cys Xaa Xaa His Cys His
1               5

<210> SEQ ID NO 108
<211> LENGTH: 22
<212> TYPE: PRT
<213> ORGANISM: Artificial Sequence
<220> FEATURE:
<223> OTHER INFORMATION: proinsulin

<400> SEQUENCE: 108

His Cys Pro Tyr Cys Val Arg Ser Leu Gln Pro Leu Ala Leu Glu Gly
1               5                   10                  15

Ser Leu Gln Lys Arg Gly
            20

<210> SEQ ID NO 109
<211> LENGTH: 24
<212> TYPE: PRT
<213> ORGANISM: Artificial Sequence
<220> FEATURE:
<223> OTHER INFORMATION: proinsulin

<400> SEQUENCE: 109

His Ala Ala Cys Pro Tyr Cys Val Arg Ser Leu Gln Pro Leu Ala Leu
1               5                   10                  15

Glu Gly Ser Leu Gln Lys Arg Gly
            20

<210> SEQ ID NO 110
<211> LENGTH: 24
<212> TYPE: PRT
<213> ORGANISM: Artificial Sequence
<220> FEATURE:
<223> OTHER INFORMATION: proinsulin

<400> SEQUENCE: 110

Ala His Ala Cys Pro Tyr Cys Val Arg Ser Leu Gln Pro Leu Ala Leu
1               5                   10                  15

Glu Gly Ser Leu Gln Lys Arg Gly
            20

<210> SEQ ID NO 111
<211> LENGTH: 24
<212> TYPE: PRT
<213> ORGANISM: Artificial Sequence
<220> FEATURE:
<223> OTHER INFORMATION: proinsulin

<400> SEQUENCE: 111

Ala Ala Ala Cys Pro Tyr Cys Val Arg Ser Leu Gln Pro Leu Ala Leu
1               5                   10                  15

Glu Gly Ser Leu Gln Lys Arg Gly
            20

<210> SEQ ID NO 112
<211> LENGTH: 24
<212> TYPE: PRT

```
<213> ORGANISM: Artificial Sequence
<220> FEATURE:
<223> OTHER INFORMATION: proinsulin

<400> SEQUENCE: 112

Ala Ala Ala Cys His Pro Cys Val Arg Ser Leu Gln Pro Leu Ala Leu
1               5                   10                  15

Glu Gly Ser Leu Gln Lys Arg Gly
            20

<210> SEQ ID NO 113
<211> LENGTH: 24
<212> TYPE: PRT
<213> ORGANISM: Artificial Sequence
<220> FEATURE:
<223> OTHER INFORMATION: proinsulin

<400> SEQUENCE: 113

Ala Ala His Cys His Pro Cys Val Arg Ser Leu Gln Pro Leu Ala Leu
1               5                   10                  15

Glu Gly Ser Leu Gln Lys Arg Gly
            20

<210> SEQ ID NO 114
<211> LENGTH: 24
<212> TYPE: PRT
<213> ORGANISM: Artificial Sequence
<220> FEATURE:
<223> OTHER INFORMATION: proinsulin

<400> SEQUENCE: 114

Ala Ala Ala Cys His Gly Cys Val Arg Ser Leu Gln Pro Leu Ala Leu
1               5                   10                  15

Glu Gly Ser Leu Gln Lys Arg Gly
            20

<210> SEQ ID NO 115
<211> LENGTH: 18
<212> TYPE: PRT
<213> ORGANISM: Artificial Sequence
<220> FEATURE:
<223> OTHER INFORMATION: mog peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 115

His Xaa Cys Pro Tyr Cys Ser Arg Val Val His Leu Tyr Arg Asn Gly
1               5                   10                  15

Lys Asp

<210> SEQ ID NO 116
<211> LENGTH: 19
<212> TYPE: PRT
<213> ORGANISM: Artificial Sequence
<220> FEATURE:
<223> OTHER INFORMATION: mog peptide
<220> FEATURE:
<221> NAME/KEY: misc_feature
<222> LOCATION: (2)..(3)
<223> OTHER INFORMATION: Xaa can be any naturally occurring amino acid
```

```
<400> SEQUENCE: 116

His Xaa Xaa Cys Pro Tyr Cys Ser Arg Val Val His Leu Tyr Arg Asn
1               5                   10                  15

Gly Lys Asp
```

IMMUNOGENIC PEPTIDES COMPRISING AN MHC CLASS II T CELL EPITOPE AND A REDOX MOTIF

CROSS-REFERENCE TO RELATED APPLICATIONS

This application is continuation of U.S. application Ser. No. 15/516,045, filed Mar. 31, 2017, which is the U.S. National Stage entry of PCT International Application No. PCT/EP2015/074063, filed Oct. 16, 2015, which claims priority to UK Patent Application No. 1418433.7, filed Oct. 17, 2014, the contents of each of which are incorporated herein by reference in their entirety.

REFERENCE TO SEQUENCE LISTING SUBMITTED ELECTRONICALLY

The content of the electronically submitted sequence listing (Name: 2752_0131_Sequence_Listing.txt; Size: 34,148 bytes; and Date of Creation: Jun. 3, 2020) filed with the application is incorporated herein by reference in its entirety.

FIELD OF THE INVENTION

The present invention relates to immunogenic peptides. The peptides are used in in vitro and in vivo systems to generate antigen specific cytolytic CD4+ T cells. The peptides and cells obtained by these peptides are used as pharmaceutically active peptides for a variety of disorders including auto immune diseases such as multiple sclerosis.

BACKGROUND OF THE INVENTION

WO2008/017517 discloses a novel class of peptides which comprise an MHC class II T cell epitope of an antigen and a redox motif sequence.

Redox motif sequences have been reviewed in Fomenko et al. (2003) *Biochemistry* 42, 11214-11225. The different alternatives of the redox motif sequence are C(X)2C [SEQ ID NO: 71], C(X)2S [SEQ ID NO: 72], C(X)2T [SEQ ID NO: 73], S(X)2C [SEQ ID NO: 74], and T(X)2C [SEQ ID NO: 75]. Other prior art on redox motif sequences comments on the relevance of a histidine within the redox motif sequence [Kortemme et al. (1996) *Biochemistry* 35, 14503-14511].

WO2008/017517 explains that the combination of a T cell epitope and a redox motif sequence in each other's proximity within a peptide provides properties which have not been recognised before. Namely, such peptides have the capacity to elicit a population of CD4+ cytolytic T cells which kill specifically the antigen presenting cells which present the antigen comprising the T cell epitope which is present in the peptide.

Consequently these peptides can be used to block an immune response at a very early stage, i.e. at the level of antigen presentation. WO2008/017517 demonstrates the medical use of these peptides in the treatment and prevention of allergies and immune disorders. The concept of the invention has been later published in Carlier et al. (2012) *Plos one* 7, 10 e45366. Further patent applications demonstrated that such peptides can be used in other medical applications wherein immune responses are to be avoided, such as the treatment of tumours, rejections of transplants, immune responses against soluble allofactors, immune responses against viral proteins encoded by the backbone of viral vectors.

The above publications discuss the type of redox motif sequence and the spacing between redox motif and T cell epitope sequence. Further determinants in the peptides which may provide improved properties to the peptides have not been reported.

SUMMARY OF THE INVENTION

The different alternatives of the 4 amino acid redox motif sequence as mentioned in the introduction can also written as [CST]-X(2)-C [SEQ ID NO: 76] or C-X(2)-[CST] [SEQ ID NO: 77]. The present invention reveals that the presence of an additional histidine amino acid immediately adjacent outside the motif (N terminal of the motif (position −1) or C-terminal of the motif (position+5)) increases the stability of the redox motif. Thus, the present invention relates to modified redox motifs with general structure or H-C-X(2)-[CST] [SEQ ID NO: 78] or [CST]-X(2)-C-H [SEQ ID NO: 79].

With this improved stability the specific reducing activity of the peptide increases, such that for example less peptide can be used or the number of injections is reduced, compared to a peptide wherein the additional histidine is not present.

A first aspect relates to isolated immunogenic peptides of between 13 and 100 amino acids comprising a MHC class II T cell epitope of an antigen, and immediately adjacent or separated by at most 7 amino acids from said epitope a H-X(0,2)-C-X(2)-[CST] ([SEQ ID NO: 78], [SEQ ID NO: 90] or [SEQ ID NO: 91]) or a [CST]-X(2)-C-X(0,2)-H ([SEQ ID NO: 79], [SEQ ID NO: 92] or [SEQ ID NO: 93]) redox motif sequence for use as a medicament.

In certain embodiment said antigen does not contain in its sequence said motif within a distance of 10 amino acids of said epitope, or even does not contain in its sequence said motif.

In specific embodiments the motif is H-X-C-X(2)-[CST] [SEQ ID NO: 90] or [CST]-X(2)-C-X-H [SEQ ID NO: 92] redox motif sequence, or is H-C-X(2)-[CST] [SEQ ID NO: 78] or [CST]-X(2)-C-H [SEQ ID NO: 79] redox motif sequence.

In other embodiments the motif is H-X(0,2)-C-X(2)-C ([SEQ ID NO: 80], [SEQ ID NO: 96] or [SEQ ID NO: 97]), or C-X(2)-C-X(0,2)-H ([SEQ ID NO: 83], [SEQ ID NO: 94] or [SEQ ID NO: 95]).

In yet other embodiments the motif is H-C-X(2)-C [SEQ ID NO: 80] or C-X(2)-C-H [SEQ ID NO: 83].

In specific embodiments, the peptides have a length of between 13 and 75 amino acids, between 13 and 50 amino acids, or between 13 and 30 amino acids.

The MHC class II T cell epitope, can separated from said motif by a sequence of at most 4 amino acids, or by a sequence of 2 amino acids.

In specific embodiments, wherein X within the redox motif is Gly or Pro, or X within the redox motif is not Cys.

In other specific embodiment, X outside the redox motif is not Cys, Ser or Thr.

The peptides can be used in the prevention or treatment of multiple sclerosis (MS), whereby the antigen is an autoantigen involved in multiple sclerosis, such as MOG.

Specific embodiments of a peptide for MS comprise the epitope sequence VVHLYRNGK [SEQ ID NO: 3], such as HCPYCSRVVHLYRNGKD [SEQ ID NO: 1], HxCPYCSRVVHLYRNGKD [SEQ ID NO: 115], or HxxCPYCSRVVHLYRNGKD [SEQ ID NO: 116].

The peptides can be used in the prevention or treatment of diabetes, wherein the antigen is for example proinsulin.

Another aspect relates to isolated immunogenic peptides of between 13 and 100 amino acids comprising a MHC class II T cell epitope of an antigen, and immediately adjacent or separated by at most 7 amino acids from said epitope a H-X(0,2)-C-X(2)-[CST] ([SEQ ID NO: 78] or [SEQ ID NO: 90] or [SEQ ID NO: 91]) or [CST]-X(2)-C-X(0,2)-H ([SEQ ID NO: 79], [SEQ ID NO: 92] or [SEQ ID NO: 93] redox motif sequence, with the proviso that said antigen does not contain in its sequence said motif within a distance of 10 amino acids of said epitope.

In certain embodiment the antigen does not contain in its sequence said motif.

Specific embodiments of motifs are H-X-C-X(2)-[CST] [SEQ ID NO: 90], [CST]-X(2)-C-X-H [SEQ ID NO: 92], H-C-X(2)-[CST] [SEQ ID NO: 78] or [CST]-X(2)-C-H [SEQ ID NO: 79], X(0,2)-C-X(2)-C([SEQ ID NO: 80], [SEQ ID NO: 96] [SEQ ID NO: 97]), C-X(2)-C-X(0,2)-H ([SEQ ID NO: 83], [SEQ ID NO: 94] [SEQ ID NO: 95]) H-C-X(2)-C [SEQ ID NO: 80] or C-X(2)-C-H [SEQ ID NO: 83].

In specific embodiments of peptides, if said motif is H-X(0,2)-C-X(2)-[CST] [SEQ ID NO: 78, 90 or 91], the motif is located N terminally from the T cell epitope within the peptide, and wherein, if said motif is [CST]-X(2)-C-X(0,2)-H [SEQ ID NO: 79, 92 or 93], the motif is located C terminally from the T cell epitope.

The motif can located N terminally from the T cell epitope. The peptides can have a length of between 13 and 75 amino acids, of between 13 and 50 amino acids, of between 13 and 30 amino acids.

In specific embodiments, the MHC class II T cell epitope, is separated from said motif by a sequence of at most 4 amino acids or is separated from said motif by sequence of 2 amino acids.

In specific embodiments X within the redox motif is Gly or Pro, or X within the redox motif is not Cys.

In specific embodiments X outside the redox motif is not Cys, Ser or Thr.

Particular peptides are from the auto-antigen is MOG or proinsulin.

Particular peptides comprise the epitope sequence VVH-LYRNGK [SEQ ID NO: 3], such as HCPYCSRVVH-LYRNGKD [SEQ ID NO: 1], HxCPYCSRVVHLYRNGKD [SEQ ID NO: 115], or HxxCPYCSRVVHLYRNGKD [SEQ ID NO: 116].

Another aspect are methods of treatment or prevention comprising the step of administering an effective amount of an immunogenic peptide of between 13 and 100 amino acids comprising an MHC class II T cell epitope of an antigen, and immediately adjacent or separated by at most 7 amino acids from said epitope a H-X(0,2)-C-X(2)-[CST] ([SEQ ID NO: 78], [SEQ ID NO: 90] or [SEQ ID NO: 91]) or a [CST]-X(2)-C-X(0,2)-H ([SEQ ID NO: 79], [SEQ ID NO: 92] or [SEQ ID NO: 93]) redox motif sequence.

Another aspect of the invention relates to in vitro use of a described above for the generation of antigen specific CD4+ cytolytic T cells.

Another aspect relates to a method for obtaining a population CD4+ T cells which are cytolytic against cells antigen, the method comprising the steps of: providing peripheral blood cells; contacting said cells in vitro with an immunogenic peptide of between 13 and 100 amino acids comprising an MHC class II T cell epitope of an antigen, and immediately adjacent or separated by at most 7 amino acids from said epitope a H-X(0,2)-C-X(2)-[CST] ([SEQ ID NO: 78], [SEQ ID NO: 90] or [SEQ ID NO: 91]) or a [CST]-X(2)-C-X(0,2)-H ([SEQ ID NO: 79], [SEQ ID NO: 92] or [SEQ ID NO: 93]) redox motif sequence; and expanding said cells in the presence of IL-2.

Another aspect relates to a population of cells obtainable by the above method of for use as a medicament.

Another aspect relates to methods of treatment and prevention comprising the step of administering an effective amount of cells as described above.

BRIEF DESCRIPTION OF THE DRAWINGS

FIG. 1: Response of naive human CD4+ T cell lines towards peptides with a T cell epitope of MOG and a redox motif without (right bars) [SEQ ID NO: 7] and with additional histidine (left bars). [SEQ ID NO: 1]

DETAILED DESCRIPTION

Definitions

The term "peptide" as used herein refers to a molecule comprising an amino acid sequence of between 2 and 200 amino acids, connected by peptide bonds, but which can comprise non-amino acid structures. Peptides according to the invention can contain any of the conventional 20 amino acids or modified versions thereof, or can contain non-naturally occurring amino-acids incorporated by chemical peptide synthesis or by chemical or enzymatic modification. The term "antigen" as used herein refers to a structure of a macromolecule, typically protein (with or without polysaccharides) or made of proteic composition comprising one or more hapten(s) and comprising T cell epitopes.

The term "antigenic protein" as used herein refers to a protein comprising one or more T cell epitopes. An auto-antigen or auto-antigenic protein as used herein refers to a human or animal protein present in the body, which elicits an immune response within the same human or animal body.

The term "food or pharmaceutical antigenic protein" refers to an antigenic protein naturally present in a food or pharmaceutical product, such as in a vaccine. The term "epitope" refers to one or several portions (which may define a conformational epitope) of an antigenic protein which is/are specifically recognised and bound by an antibody or a portion thereof (Fab', Fab2', etc.) or a receptor presented at the cell surface of a B or T cell lymphocyte, and which is able, by said binding, to induce an immune response. The term "T cell epitope" in the context of the present invention refers to a dominant, sub-dominant or minor T cell epitope, i.e. a part of an antigenic protein that is specifically recognised and bound by a receptor at the cell surface of a T lymphocyte. Whether an epitope is dominant, sub-dominant or minor depends on the immune reaction elicited against the epitope. Dominance depends on the frequency at which such epitopes are recognised by T cells and able to activate them, among all the possible T cell epitopes of a protein.

The T cell epitope is an epitope recognised by MHC class II molecules, which consists of a sequence of +/−9 amino acids which fit in the groove of the MHC II molecule. Within a peptide sequence representing a T cell epitope, the amino acids in the epitope are numbered P1 to P9, amino acids N-terminal of the epitope are numbered P−1, P−2 and so on, amino acids C terminal of the epitope are numbered P+1, P+2 and so on. Peptides recognised by MHC class II molecules and not by MHC class I molecules are referred to as MHC class II restricted T cell epitopes.

The term "MHC" refers to "major histocompatibility antigen". In humans, the MHC genes are known as HLA ("human leukocyte antigen") genes. Although there is no consistently followed convention, some literature uses HLA to refer to HLA protein molecules, and MHC to refer to the genes encoding the HLA proteins. As such the terms "MHC" and "HLA" are equivalents when used herein. The HLA system in man has its equivalent in the mouse, i.e., the H2 system. The most intensely-studied HLA genes are the nine so-called classical MHC genes: HLA-A, HLA-B, HLA-C, HLA-DPA1, HLA-DPB1, HLA-DQA1, HLAs DQB1, HLA-DRA, and HLA-DRB1. In humans, the MHC is divided into three regions: Class I, II, and III. The A, B, and C genes belong to MHC class I, whereas the six D genes belong to class II. MHC class I molecules are made of a single polymorphic chain containing 3 domains (alpha 1, 2 and 3), which associates with beta 2 microglobulin at cell surface. Class II molecules are made of 2 polymorphic chains, each containing 2 chains (alpha 1 and 2, and beta 1 and 2).

Class I MHC molecules are expressed on virtually all nucleated cells.

Peptide fragments presented in the context of class I MHC molecules are recognised by CD8+ T lymphocytes (cytolytic T lymphocytes or CTLs). CD8+ T lymphocytes frequently mature into cytolytic effectors which can lyse cells bearing the stimulating antigen. Class II MHC molecules are expressed primarily on activated lymphocytes and antigen-presenting cells. CD4+ T lymphocytes (helper T lymphocytes or Th) are activated with recognition of a unique peptide fragment presented by a class II MHC molecule, usually found on an antigen-presenting cell like a macrophage or dendritic cell. CD4+ T lymphocytes proliferate and secrete cytokines such as IL-2, IFN-gamma and IL-4 that support antibody-mediated and cell mediated responses.

Functional HLAs are characterised by a deep binding groove to which endogenous as well as foreign, potentially antigenic peptides bind. The groove is further characterised by a well-defined shape and physico-chemical properties. HLA class I binding sites are closed, in that the peptide termini are pinned down into the ends of the groove. They are also involved in a network of hydrogen bonds with conserved HLA residues. In view of these restraints, the length of bound peptides is limited to 8-10 residues. However, it has been demonstrated that peptides of up to 12 amino acid residues are also capable of binding HLA class I. Comparison of the structures of different HLA complexes confirmed a general mode of binding wherein peptides adopt a relatively linear, extended conformation, or can involve central residues to bulge out of the groove.

In contrast to HLA class I binding sites, class II sites are open at both ends. This allows peptides to extend from the actual region of binding, thereby "hanging out" at both ends. Class II HLAs can therefore bind peptide ligands of variable length, ranging from 9 to more than 25 amino acid residues. Similar to HLA class I, the affinity of a class II ligand is determined by a "constant" and a "variable" component. The constant part again results from a network of hydrogen bonds formed between conserved residues in the HLA class II groove and the main-chain of a bound peptide. However, this hydrogen bond pattern is not confined to the N- and C-terminal residues of the peptide but distributed over the whole chain. The latter is important because it restricts the conformation of complexed peptides to a strictly linear mode of binding. This is common for all class II allotypes.

The second component determining the binding affinity of a peptide is variable due to certain positions of polymorphism within class II binding sites. Different allotypes form different complementary pockets within the groove, thereby accounting for subtype-dependent selection of peptides, or specificity. Importantly, the constraints on the amino acid residues held within class II pockets are in general "softer" than for class I. There is much more cross reactivity of peptides among different HLA class II allotypes. The sequence of the +/−9 amino acids of an MHC class II T cell epitope that fit in the groove of the MHC II molecule are usually numbered P1 to P9. Additional amino acids N-terminal of the epitope are numbered P−1, P−2 and so on, amino acids C-terminal of the epitope are numbered P+1, P+2 and so on.

The term "homologue" as used herein with reference to the epitopes used in the context of the invention, refers to molecules having at least 50%, at least 70%, at least 80%, at least 90%, at least 95% or at least 98% amino acid sequence identity with the naturally occurring epitope, thereby maintaining the ability of the epitope to bind an antibody or cell surface receptor of a B and/or T cell. Particular homologues of an epitope correspond to the natural epitope modified in at most three, more particularly in at most 2, most particularly in one amino acid.

The term "derivative" as used herein with reference to the peptides of the invention refers to molecules which contain at least the peptide active portion (i.e. capable of eliciting cytolytic CD4+ T cell activity) and, in addition thereto comprises a complementary portion which can have different purposes such as stabilising the peptides or altering the pharmacokinetic or pharmacodynamic properties of the peptide.

The term "sequence identity" of two sequences as used herein relates to the number of positions with identical nucleotides or amino acids divided by the number of nucleotides or amino acids in the shorter of the sequences, when the two sequences are aligned. In particular, the sequence identity is from 70% to 80%, from 81% to 85%, from 86% to 90%, from 91% to 95%, from 96% to 100%, or 100%.

The terms "peptide-encoding polynucleotide (or nucleic acid)" and "polynucleotide (or nucleic acid) encoding peptide" as used herein refer to a nucleotide sequence, which, when expressed in an appropriate environment, results in the generation of the relevant peptide sequence or a derivative or homologue thereof. Such polynucleotides or nucleic acids include the normal sequences encoding the peptide, as well as derivatives and fragments of these nucleic acids capable of expressing a peptide with the required activity.

The nucleic acid encoding a peptide according to the invention or fragment thereof is a sequence encoding the peptide or fragment thereof originating from a mammal or corresponding to a mammalian, most particularly a human peptide fragment.

The term "immune disorders" or "immune diseases" refers to diseases wherein a reaction of the immune system is responsible for or sustains a malfunction or non-physiological situation in an organism. Included in immune disorders are, inter alia, allergic disorders and autoimmune diseases.

The terms "allergic diseases" or "allergic disorders" as used herein refer to diseases characterised by hypersensitivity reactions of the immune system to specific substances called allergens (such as pollen, stings, drugs, or food). Allergy is the ensemble of signs and symptoms observed whenever an atopic individual patient encounters an allergen to which he has been sensitised, which may result in the development of various diseases, in particular respiratory diseases and symptoms such as bronchial asthma. Various types of classifications exist and mostly allergic disorders have different names depending upon where in the mammalian body it occurs. "Hypersensitivity" is an undesirable (damaging, discomfort-producing and sometimes fatal) reaction produced in an individual upon exposure to an antigen to which it has become sensitised; "immediate hypersensitivity" depends of the production of lgE antibodies and is therefore equivalent to allergy.

The terms "autoimmune disease" or "autoimmune disorder" refer to diseases that result from an aberrant immune response of an organism against its own cells and tissues due to a failure of the organism to recognise its own constituent parts (down to the sub-molecular level) as "self". The group of diseases can be divided in two categories, organ-specific and systemic diseases. An "allergen" is defined as a substance, usually a macromolecule or a proteic composition which elicits the production of lgE antibodies in predisposed, particularly genetically disposed, individuals (atopics) patients. Similar definitions are presented in Liebers et al. (1996) *Clin. Exp. Allergy* 26, 494-516.

The term "therapeutically effective amount" refers to an amount of the peptide of the invention or derivative thereof, which produces the desired therapeutic or preventive effect in a patient. For example, in reference to a disease or disorder, it is the amount which reduces to some extent one or more symptoms of the disease or disorder, and more particularly returns to normal, either partially or completely, the physiological or biochemical parameters associated with or causative of the disease or disorder. Typically, the therapeutically effective amount is the amount of the peptide of the invention or derivative thereof, which will lead to an improvement or restoration of the normal physiological situation. For instance, when used to therapeutically treat a mammal affected by an immune disorder, it is a daily amount peptide/kg body weight of the said mammal. Alternatively, where the administration is through gene-therapy, the amount of naked DNA or viral vectors is adjusted to ensure the local production of the relevant dosage of the peptide of the invention, derivative or homologue thereof.

The term "natural" when referring to a peptide relates to the fact that the sequence is identical to a fragment of a naturally occurring protein (wild type or mutant). In contrast therewith the term "artificial" refers to a sequence which as such does not occur in nature. An artificial sequence is obtained from a natural sequence by limited modifications such as changing/deleting/inserting one or more amino acids within the naturally occurring sequence or by adding/removing amino acids N- or C-terminally of a naturally occurring sequence.

In this context, it is realised that peptide fragments are generated from antigens, typically in the context of epitope scanning. By coincidence such peptides may comprise in their sequence an MHC class II epitope and in their proximity a sequence with the modified redox motif H-X(0,2)-C-X(2)-[CST] [SEQ ID NO: 78, 90 or 91] or [CST]-X(2)-C-X(0,2)-H [SEQ ID NO: 79, 92 or 93]. Herein "proximity" means that between MHC class II epitope sequence and between the above H-X(0,2)-C-X(2)-[CST] [SEQ ID NO: 78, 90 or 91] or [CST]-X(2)-C-X(0,2)-H [SEQ ID NO: 79, 92 or 93] motifs, there can be an amino acid sequence of at most 7 amino acids, at most 4 amino acids, at most 2 amino acids, or even 0 amino acids (in other word epitope and motif sequence are immediately adjacent to each other).

Accordingly, specific embodiments of the present invention exclude peptide fragments of antigens which accidentally comprise as well an MHC class T cell and a redox motif sequence immediately adjacent to each other or separated by an amino acid sequence of up to 2, 4 or 7 amino acids.

Other specific embodiments of the present invention exclude peptide fragments of antigens which accidentally comprise as well an MHC class II T cell epitope and a redox motif sequence, regardless from the spacing between epitope and motif modified redox motif.

Peptide fragments of antigens are studied for the immunogenic properties but are generally not used a therapeutic agent (apart from the field of allergy and tumour vaccination). Thus in the absence of any knowledge of the improved properties of the peptides of the present invention the use of such peptides as medicaments is unprecedented Amino acids are referred to herein with their full name, their three-letter abbreviation or their one letter abbreviation.

Motifs of amino acid sequences are written herein according to the format of Prosite. Motifs are used to describe a certain sequence variety at specific parts of a sequence. The symbol X is used for a position where any amino acid is accepted. Alternatives are indicated by listing the acceptable amino acids for a given position, between square brackets ('[ ]'). For example: [CST] stands for an amino acid selected from Cys, Ser or Thr. Amino acids which are excluded as alternatives are indicated by listing them between curly brackets ('{ }'). For example: {AM} stands for any amino acid except Ala and Met. The different elements in a motif are separated from each other by a hyphen -.Repetition of an identical element within a motif can be indicated by placing behind that element a numerical value or a numerical range between parentheses. For example: X(2) corresponds to X-X; X(2, 5) corresponds to 2, 3, 4 or 5 X amino acids, A(3) corresponds to A-A-A.

Thus, H-C-X(2)-C [SED ID NO: 80] can be written as HCXXC [SED ID NO: 80].

Equally C-X(2)-C-X(0,2) represents the three possibilities wherein there is between H and C, none, one or two amino acids; namely CXXCH [SEQ ID NO: 83], CXXCXH [SEQ ID NO: 94] and CXXCXXH [SEQ ID NO: 95].

Equally H-X(0,2)-C-X(2)-C represents the three possibilities wherein there is between H and C, none, one or two amino acids. Namely HCXXC [SEQ ID NO: 80], HXCXXC [SEQ ID NO: 96] and HXXCXXC [SEQ ID NO: 97]

To distinguish between the amino acids X, those between H and C are called external amino acids X (single underlined in the above sequence), those within the redox motif are called internal amino acids X (double underlined in the above sequence).

X represents any amino acid, particularly an L-amino acid, more particularly one of the 20 naturally occurring L-amino acids.

A peptide, comprising a T cell epitope and a modified peptide motif sequence, having reducing activity is capable of generating a population of antigen-specific cytolytic CD4+ T cell towards antigen-presenting cells.

Accordingly, in its broadest sense, the invention relates to peptides which comprise at least one T-cell epitope of an antigen (self or non-self) with a potential to trigger an immune reaction, and a modified thioreductase sequence motif with a reducing activity on peptide disulfide bonds. The T cell epitope and the modified redox motif sequence may be immediately adjacent to each other in the peptide or optionally separated by a one or more amino acids (so called linker sequence). Optionally the peptide additionally comprises an endosome targeting sequence and/or additional "flanking" sequences.

The peptides of the invention comprise an MHC class II T-cell epitope of an antigen (self or non-self) with a potential to trigger an immune reaction, and a modified redox motif. The reducing activity of the motif sequence in the peptide can be assayed for its ability to reduce a sulfhydryl group such as in the insulin solubility assay wherein the solubility of insulin is altered upon reduction, or with a fluorescence-labelled substrate such as insulin. An example of such assay is described in more detail in the experimental section of this application.

The modified redox motif may be positioned at the amino-terminus side of the T-cell epitope or at the carboxy-terminus of the T-cell epitope.

Peptide fragments with reducing activity are encountered in thioreductases which are small disulfide reducing enzymes including glutaredoxins, nucleoredoxins, thioredoxins and other thiol/disulfide oxydoreductases (Holmgren (2000) *Antioxid. Redox Signal.* 2, 811-820; Jacquot et al. (2002) *Biochem. Pharm.* 64, 1065-1069). They are multifunctional, ubiquitous and found in many prokaryotes and eukaryotes. They exert reducing activity for disulfide bonds on proteins (such as enzymes) through redox active cysteines within conserved active domain consensus sequences: C-X(2)-C [SEQ ID NO: 71], C-X(2)-S [SEQ ID NO: 72], C-X(2)-T [SEQ ID NO: 73], S-X(2)-C [SEQ ID NO: 74], T-X(2)-C [SEQ ID NO: 75] (Fomenko et al. (2003) *Biochemistry* 42, 11214-11225; Fomenko et al. (2002) *Prot. Science* 11, 2285-2296), in which X stands for any amino acid. Such domains are also found in larger proteins such as protein disulfide isomerase (PDI) and phosphoinositide-specific phospholipase C.

The 4 amino acid redox motif as known from e.g. Fomenko and WO2008/017517 comprises a cysteine at position 1 and/or 4; thus the motif is either C-X(2)-[CST] [SEQ ID NO: 77] or [CST]-X(2)-C [SEQ ID NO: 76]. Such a tetrapeptide sequence will be referred to as "the motif". The motif in a peptide can be any of the alternatives C-X(2)-C [SEQ ID NO: 71], S-X(2)-C [SEQ ID NO: 74], T-X(2)-C [SEQ ID NO: 75], C-X(2)-S [SEQ ID NO: 72] or C-X(2)-T [SEQ ID NO: 73]. In particular, peptides contain the sequence motif C-X(2)-C [SEQ ID NO: 71].

The "modified" redox motif of the peptides of the present invention differs from the prior art in that immediately adjacent cysteine and outside the motif a histidine is present, in other words the modified redox motif is written as H-X(0,2)-C-X(2)-[CST] [SEQ ID NO: 78, 90 or 91] or [CST]-X(2)-C-X(0,2)-H [SEQ ID NO: 79, 92 or 93].

Embodiments hereof are H-XX-C-X(2)-[CST] [SEQ ID NO: 91], H-X-C-X(2)-[CST] [SEQ ID NO: 90], H-C-X(2)-[CST] [SEQ ID NO: 78], [CST]-X(2)-C—XX-H [SEQ ID NO: 93] [CST]-X(2)-C-X-H [SEQ ID NO: 92], and [CST]-X(2)-C-H [SEQ ID NO: 79], More specific embodiments are

H-C-X(2)-S, [SEQ ID NO: 81]

H-X-C-X(2)-S, [SEQ ID NO: 98]

H-XX-C-X(2)-S, [SEQ ID NO: 99]

H-C-X(2)-T, [SEQ ID NO: 82]

H-X-C-X(2)-T, [SEQ ID NO: 100]

H-XX-C-X(2)-T, [SEQ ID NO: 101]

S-X(2)-C-H, [SEQ ID NO: 84]

S-X(2)-C-X-H, [SEQ ID NO: 102]

S-X(2)-CXX-H, [SEQ ID NO: 103]

T-X(2)-C-H, [SEQ ID NO: 85]

T-X(2)-C-X-H, [SEQ ID NO: 104]

T-X(2)-C-XX-H, [SEQ ID NO: 105]

C-X(2)-C-H, [SEQ ID NO: 83]

C-X(2)-C-X-H, [SEQ ID NO: 94]

C-X(2)-C-XX-H, [SEQ ID NO: 95]

H-C-X(2)-C, [SEQ ID NO: 80]

H-X-C-X(2)-C, [SEQ ID NO: 96]

H-XX- C-X(2)-C. [SEQ ID NO: 97]

In specific embodiments of the invention peptides with a H-C-X(2)-C-H [SEQ ID NO: 86] motif are excluded from the scope of the invention.

Other specific embodiments are peptides wherein a cysteine amino acid of the redox motif is flanked by two histidine sequences such as HCHxC [SEQ ID NO: 106] or CxxHCH [SEQ ID NO: 107].

As explained in detail further on, the peptides of the present invention can be made by chemical synthesis, which allows the incorporation of non-natural amino acids. Accordingly, "C" in the above recited redox modified redox motifs represents either cysteine or another amino acids with a thiol group such as mercaptovaline, homocysteine or other natural or non-natural amino acids with a thiol function. In order to have reducing activity, the cysteines present in a modified redox motif should not occur as part of a cystine disulfide bridge. Nevertheless, a redox modified redox motif may comprise modified cysteines such as methylated cysteine, which is converted into cysteine with free thiol groups in vivo. X can be any of the 20 natural amino acids, including S, C, or T or can be a non-natural amino acid. In particular embodiments X is an amino acid with a small side chain such as Gly, Ala, Ser or Thr. In further particular embodiments, X is not an amino acid with a bulky side chain such as Trp. In further particular embodiments X is not cysteine. In further particular embodiments at least one X in the modified redox motif is His. In other further particular embodiments at least one X in the modified redox is Pro.

Peptides may further comprise modifications to increase stability or solubility, such as modification of the N-terminal $NH_2$ group or the C terminal COOH group (e.g. modification of the COOH into a $CONH_2$ group).

In the peptides of the present invention comprising a modified redox motif, the motif is located such that, when the epitope fits into the MHC groove, the motif remains outside of the MHC binding groove. The modified redox motif is placed either immediately adjacent to the epitope sequence within the peptide [in other words a linker sequence of zero amino acids between motif and epitope], or is separated from the T cell epitope by a linker comprising an amino acid sequence of 7 amino acids or less. More particularly, the linker comprises 1, 2, 3, or 4 amino acids. Specific embodiments are peptides with a 0, 1 or 2 amino acid linker between epitope sequence and modified redox motif sequence. Alternatively, a linker may comprise 5, 6, 7, 8, 9 or 10 amino acids. In those peptides where the modified redox motif sequence is adjacent to the epitope sequence this is indicated as position P−4 to P−1 or P+1 to P+4 compared to the epitope sequence. Apart from a peptide linker, other organic compounds can be used as linker to link the parts of the peptide to each other (e.g. the modified redox motif sequence to the T cell epitope sequence).

The peptides of the present invention can further comprise additional short amino acid sequences N or C-terminally of the sequence comprising the T cell epitope and the modified redox motif. Such an amino acid sequence is generally referred to herein as a ‘flanking sequence’. A flanking sequence can be positioned between the epitope and an endosomal targeting sequence and/or between the modified redox motif and an endosomal targeting sequence. In certain peptides, not comprising an endosomal targeting sequence, a short amino acid sequence may be present N and/or C terminally of the modified redox motif and/or epitope sequence in the peptide. More particularly a flanking sequence is a sequence of between 1 and 7 amino acids, most particularly a sequence of 2 amino acids.

The modified redox motif may be located N-terminal from the epitope.

In certain embodiments, wherein the modified redox motif contains one cysteine, this cysteine is present in the modified redox motif in the position remote from the epitope, thus the modified redox motif occurs for example as H-C-X(2)-T [SEQ ID NO: 82] or H-C-X(2)-S [SEQ ID NO: 81] N-terminally of the epitope or occurs as T-X(2)-C-H [SEQ ID NO: 85] or S-X(2)-C-H [SEQ ID NO: 84] C-terminally of the epitope.

In certain embodiments of the present invention, peptides are provided comprising one epitope sequence and a modified redox motif sequence. In further particular embodiments, the modified redox motif occurs several times (1, 2, 3, 4 or even more times) in the peptide, for example as repeats of the modified redox motif which can be spaced from each other by one or more amino acids or as repeats which are immediately adjacent to each other. Alternatively, one or more modified redox motifs are provided at both the N and the C terminus of the T cell epitope sequence.

Other variations envisaged for the peptides of the present invention include peptides which contain repeats of a T cell epitope sequence wherein each epitope sequence is preceded and/or followed by the modified redox motif (e.g. repeats of “modified redox motif-epitope” or repeats of “modified redox motif-epitope-modified redox motif”). Herein the modified redox motifs can all have the same sequence but this is not obligatory. It is noted that repetitive sequences of peptides which comprise an epitope which in itself comprises the modified redox motif will also result in a sequence comprising both the ‘epitope’ and a ‘modified redox motif’. In such peptides, the modified redox motif within one epitope sequence functions as a modified redox motif outside a second epitope sequence.

Typically the peptides of the present invention comprise only one T cell epitope. As described below a T cell epitope in a protein sequence can be identified by functional assays and/or one or more in silica prediction assays. The amino acids in a T cell epitope sequence are numbered according to their position in the binding groove of the MHC proteins. A T-cell epitope present within a peptide consist of between 8 and 25 amino acids, yet more particularly of between 8 and 16 amino acids, yet most particularly consists of 8, 9, 10, 11, 12, 13, 14, 15 or 16 amino acids.

In a more particular embodiment, the T cell epitope consists of a sequence of 9 amino acids. In a further particular embodiment, the T-cell epitope is an epitope, which is presented to T cells by MHC-class II molecules [MHC class II restricted T cell epitopes]. Typically T cell epitope sequence refers to the octapeptide or more specifically nonapeptide sequence which fits into the cleft of an MHC TT protein.

The T cell epitope of the peptides of the present invention can correspond either to a natural epitope sequence of a protein or can be a modified version thereof, provided the modified T cell epitope retains its ability to bind within the MHC cleft, similar to the natural T cell epitope sequence. The modified T cell epitope can have the same binding affinity for the MHC protein as the natural epitope, but can also have a lowered affinity. In particular, the binding affinity of the modified peptide is no less than 10-fold less than the original peptide, more particularly no less than 5 times less. Peptides of the present invention have a stabilising effect on protein complexes. Accordingly, the stabilising effect of the peptide-MHC complex compensates for the lowered affinity of the modified epitope for the MHC molecule.

The sequence comprising the T cell epitope and the reducing compound within the peptide can be further linked to an amino acid sequence (or another organic compound) that facilitates uptake of the peptide into late endosomes for processing and presentation within MHC class II determinants. The late endosome targeting is mediated by signals present in the cytoplasmic tail of proteins and correspond to well-identified peptide motifs such as the dileucine-based [DE]XXXL[LI] [SEQ ID NO: 87] or DXXLL [SEQ ID NO: 88] motif, the tyrosine-based YXXD [SEQ ID NO: 89] motif or the so called acidic cluster motif. The symbol (D represents amino acid residues with a bulky hydrophobic side chains such as Phe, Tyr and Trp. The late endosome targeting sequences allow for processing and efficient presentation of the antigen-derived T cell epitope by MHC-class II molecules. Such endosomal targeting sequences are contained, for example, within the gp75 protein (Vijayasaradhi et al. (1995) *J. Cell. Biol.* 130, 807-820), the human CD3 gamma protein, the HLA-BM 11 (Copier et al. (1996) *J. Immunol.* 157, 1017-1027), the cytoplasmic tail of the DEC205 receptor (Mahnke et al. (2000) *J Cell Biol.* 151, 673-683). Other examples of peptides which function as sorting signals to the endosome are disclosed in the review of Bonifacio and Traub (2003)*Annu. Rev. Biochem.* 72, 395-447. Alternatively, the sequence can be that of a subdominant or minor T cell epitope from a protein, which facilitates uptake in late endosome without overcoming the T cell response towards the antigen. The late endosome targeting sequence can be located either at the amino-terminal or at the carboxy-terminal end of the antigen derived peptide for efficient uptake and processing and can also be coupled through a flanking sequence, such as a peptide sequence of up to 10 amino acids. When using a minor T cell epitope for targeting purpose, the latter is typically located at the amino-terminal end of the antigen derived peptide.

Accordingly, the present invention envisages peptides of antigenic proteins and their use in eliciting specific immune reactions. These peptides can either correspond to fragments of proteins which comprise, within their sequence i.e. a reducing compound and a T cell epitope separated by at most 10, preferably 7 amino acids or less. Alternatively, and for most antigenic proteins, the peptides of the invention are generated by coupling a reducing compound, more particularly a reducing modified redox motif as described herein, N-terminally or C-terminally to a T cell epitope of the antigenic protein (either directly adjacent thereto or with a linker of at most 10, more particularly at most 7 amino acids). Moreover the T cell epitope sequence of the protein and/or the modified redox motif can be modified and/or one or more flanking sequences and/or a targeting sequence can be introduced (or modified), compared to the naturally occurring sequence. Thus, depending on whether or not the features of the present invention can be found within the sequence of the antigenic protein of interest, the peptides of the present invention can comprise a sequence which is 'artificial' or 'naturally occurring'.

The peptides of the present invention can vary substantially in length. The length of the peptides can vary from 13 or 14 amino acids, i.e. consisting of an epitope of 8-9 amino acids, adjacent thereto the modified redox motif 5 amino acids with the histidine, up to 20, 25, 30, 40, 50, 75, 100 or 200 amino acids. For example, a peptide may comprise an endosomal targeting sequence of 40 amino acids, a flanking sequence of about 2 amino acids, a motif as described herein of 5 amino acids, a linker of 4 amino acids and a T cell epitope peptide of 9 amino acids.

Accordingly, in particular embodiments, the complete peptides consist of between 13 amino acids up to 50, 75, 100 or 200 amino acids. More particularly, where the reducing compound is a modified redox motif as described herein, the length of the (artificial or natural) sequence comprising the epitope and modified redox motif optionally connected by a linker (referred to herein as 'epitope-modified redox motif' sequence), without the endosomal targeting sequence, is critical. The 'epitope-modified redox motif' more particularly has a length of 13, 14, 15, 16, 17, 18 or 19 amino acids. Such peptides of 13 or 14 to 19 amino acids can optionally be coupled to an endosomal targeting signal of which the size is less critical.

As detailed above, in particular embodiments, the peptides of the present invention comprise a reducing modified redox motif as described herein linked to a T cell epitope sequence.

A small number of protein sequences, fragments of proteins or synthetic peptides may by coincidence comprise a modified redox motif sequence. However the chance that these proteins comprise a MHC class T cell epitope in the proximity of the modified redox sequence becomes very small. If existing such peptides will be probably known from epitope scanning experiments wherein sets of overlapping peptide fragments are synthesised. In such publications the interest goes to the epitope and neglect the relevance of a modified redox motif with a histidine and the relevance of such peptides in medical applications.

Such peptides are thus accidental disclosures unrelated to the inventive concept of the present invention.

In further particular embodiments, the peptides of the invention are peptides comprising T cell epitopes which do not comprise an amino acid sequence with redox properties within their natural sequence.

However, in alternative embodiments, the T cell epitope may comprise any sequence of amino acids ensuring the binding of the epitope to the MHC cleft. Where an epitope of interest of an antigenic protein comprises a modified redox motif such as described herein within its epitope sequence, the immunogenic peptides according to the present invention comprise the sequence of a modified redox motif as described herein and/or of another reducing sequence coupled N- or C-terminally to the epitope sequence such that (contrary to the modified redox motif present within the epitope, which is buried within the cleft) the attached modified redox motif can ensure the reducing activity.

Accordingly the T cell epitope and motif are immediately adjacent or separated from each other and do not overlap. To assess the concept of "immediately adjacent" or "separated", the 8 or 9 amino acid sequence which fits in the MHC cleft is determined and the distance between this octapeptide or nonapeptide with the modified redox motif pentapeptide is determined.

Generally, the peptides of the present invention are not natural (thus no fragments of proteins as such) but artificial peptides which contain, in addition to a T cell epitope, a modified redox motif as described herein, whereby the modified redox motif is immediately separated from the T cell epitope by a linker consisting of up to seven, most particularly up to four or up to 2 amino acids.

It has been shown that upon administration (i.e. injection) to a mammal of a peptide according to the invention (or a composition comprising such a peptide), the peptide elicits the activation of T cells recognising the antigen derived T cell epitope and provides an additional signal to the T cell through reduction of surface receptor. This supra-optimal activation results in T cells acquiring cytolytic properties for the cell presenting the T cell epitope, as well as suppressive properties on bystander T cells. In this way, the peptides or composition comprising the peptides described in the present invention, which contain an antigen-derived T cell epitope and, outside the epitope, a modified redox motif can be used for direct immunisation of mammals, including human beings. The invention thus provides peptides of the invention or derivatives thereof, for use as a medicine. Accordingly, the present invention provides therapeutic methods which comprise administering one or more peptides according to the present invention to a patient in need thereof.

The present invention offers methods by which antigen-specific T cells endowed with cytolytic properties can be elicited by immunisation with small peptides. It has been found that peptides which contain (i) a sequence encoding a T cell epitope from an antigen and (ii) a consensus sequence with redox properties, and further optionally also comprising a sequence to facilitate the uptake of the peptide into late endosomes for efficient MHC-class II presentation, elicit suppressor T-cells.

The immunogenic properties of the peptides of the present invention are of particular interest in the treatment and prevention of immune reactions.

Peptides described herein are used as medicament, more particularly used for the manufacture of a medicament for the prevention or treatment of an immune disorder in a mammal, more in particular in a human.

The present invention describes methods of treatment or prevention of an immune disorder of a mammal in need for such treatment or prevention, by using the peptides of the invention, homologues or derivatives thereof, the methods comprising the step of administering to said mammal suffering or at risk of an immune disorder a therapeutically effective amount of the peptides of the invention, homologues or derivatives thereof such as to reduce the symptoms of the immune disorder. The treatment of both humans and animals, such as, pets and farm animals is envisaged. In an embodiment the mammal to be treated is a human. The immune disorders referred to above are in a particular embodiment selected from allergic diseases and autoimmune diseases. Allergic diseases are conventionally described as type-1 mediated diseases or lgE-mediated diseases. Clinical manifestations of allergic diseases include bronchial asthma, allergic rhinitis, atopic dermatitis, food hypersensitivity and anaphylactic reactions to insect bites or drugs. Allergic diseases are caused by hypersensitivity reactions of the immune system to specific substances called allergens (such as pollen, stings, drugs, or food). The most severe form of an allergic disorder is anaphylactic shock, which is a medical emergency. Allergens include airborne allergens, such as those of house dust mite, pets and pollens.

Allergens also include ingested allergens responsible for food hypersensitivity, including fruits, vegetables and milk. In order to treat the above diseases, peptides according to the invention are generated from the antigenic proteins or allergens known or believed to be a causative factor of the disease. The allergens that can be used for selection of T-cell epitopes are typically allergens which are selected from the group consisting of: food allergens present in peanuts, fish e.g. codfish, egg white, crustacean e.g. shrimp, milk e.g. cow's milk, wheat, cereals, fruits of the Rosacea family (apple, plum, strawberry), vegetables of the Liliacea, Cruciferae, Solanaceae and Umbelliferae families, tree nuts, sesame, peanut, soybean and other legume family allergens, spices, melon, avocado, mango, fig, banana, . . . house dust mites allergens obtained from *Dermatophagoides* spp or *D. pteronyssinus, D. farinae* and *D. microceras, Euroglyphus maynei* or *Blomia* sp., allergens from insects present in cockroach or Hymenoptera, allergens from pollen, especially pollens of tree, grass and weed, allergens from animals, especially in cat, dog, horse and rodent, allergens from fungi, especially from *Aspergillus, Alternaria* or *Cladosporium*, and occupational allergens present in products such as latex, amylase, etc. As an example on allergens, in the context of the present invention the derp 2 peptide CGFSSNYCQIYPPNANKIR [SEQ ID NO: 9] is modified in HCGFSSNYCQIYPPNANKIR [SEQ ID NO: 10] or HCGFCSNYCQIYPPNANKIR [SEQ ID NO: 11]. As a further example on allergens the der p 2 peptide CHGSEPCIIHRGKPF [SEQ ID NO: 12], is modified into HCHGSEPCIIHRGKPF [SEQ ID NO: 13], HCHGCEPCIIHRGKPF [SEQ ID NO: 14] more typically into HCxGSEPCIIHRGKPF [SEQ ID NO: 15] or HCxGCEPCIIHRGKPF wherein x is not His or Cys [SEQ ID NO: 16].

As a further example on allergens the Beta lactoglobulin peptide CHGCAQKKIIAEK [SEQ ID NO: 17] is modified into HCHGCAQKKIIAEK [SEQ ID NO: 18], more typically into HCxGCAQKKIIAEK, wherein x is not Cys or His [SEQ ID NO: 19].

As an example on auto-immune disease the thyroid peroxidase peptide CGPCMNEELTERL [SEQ ID NO: 20] is modified into HCGPCMNEELTERL [SEQ ID NO: 21].

As an example on auto-immune disease the thyroglobulin peptide CGPSAALTWVQTH [SEQ ID NO: 22] is modified into HCGPCAALTWVQTH [SEQ ID NO: 23].

The present invention further relates to peptides with the modified redox motif comprising MHC class II T cell epitopes of viral proteins which are encoded via the backbone of viral vectors used in gene therapy and gene vaccination. The present invention further relates to methods of treatment or prevention of immunogenic response against a viral vector. Examples of viral vectors (e.g. from adenovirus, adeno-associated virus, herpes virus or poxvirus, retroviruses or lentivirus) and viral proteins (e.g. capsid protein) are disclosed in WO2009101204.

As an example of the teaching of the present invention, the adenoviral peptide CHGCPTLLYVLFEV [SEQ ID NO: 24] is modified into HCHGCPTLLYVLFEV [SEQ ID NO: 25], more typical HCxGCPTLLYVLFEV wherein X is not Cys or His [SEQ ID NO: 26]

As a further example, adenoviral late protein 2 peptide CGPCGGYVPFHIQVP [SEQ ID NO: 27] is modified into HCGPCGGYVPFHIQVP [SEQ ID NO: 28].

The present invention further relates to peptides with the modified redox motif comprising MHC class II T cell epitopes of proteins of intracellular pathogens. The present invention further relates to methods of treatment and prevention of infections with intracellular pathogens. Examples of intracellular pathogens (viruses [DNA vs RNA viruses, ss vs ds viruses, bacteria, mycobacteria or parasites with an intracellular life cycle) and antigens are discussed in WO2009101208 (for example Herpesviridae, Flaviviridae and Picomaviridae, influenza, measles and immunodeficiency viruses, papilloviruses. Bacteria and mycobacteria including *Mycobacterium tuberculosis*, and other mycobacteria pathogenic for humans or animals such as Yersiniae, Brucellae, Chlamydiae, Mycoplasmae, Rickettsiae, Salmonellae and Shigellae. Parasites include Plasmodiums, Leishmanias, Trypanosomas, *Toxoplasma gondii, Listeria* sp., *Histoplasma* sp.

As a further example the CSP antigen of malaria CGHCDKHIEQYLK [SEQ ID NO: 29] is modified into HCGHCDKHIEQYLK [SEQ ID NO: 30], more typical into HCGxCDKHIEQYLK, wherein x is not Cys or His [SEQ ID NO: 31].

As a further example the CGHCEKKICKMEK [SEQ ID NO: 32]. peptide of the same antigen is modified into HCGHCEKKICKMEK [SEQ ID NO: 33], more typically into HCGxCEKKICKMEK [SEQ ID NO: 34], wherein x is not Cys or His.

As a further example the peptide from influenza hemagglutinin is modified from CGHCKYVKQNTLK [SEQ ID NO: 35] into HCGHCKYVKQNTLK [SEQ ID NO: 36], more typically into HCGxCKYVKQNTLK, wherein x is not Cys or His [SEQ ID NO: 37].

As a further example the peptide from *Leishmania* Lack antigen CGHCEHPIVVSGS [SEQ ID NO: 38] is modified into HCGHCEHPIVVSGS [SEQ ID NO: 39], more typical HCGxCEHPIVVSGS, wherein X is not Cys or His [SEQ ID NO: 40].

As a further example the peptide of the gp120 subunit of the Env protein of HIV, is modified from CGHCRAMYAPPIA [SEQ ID NO: 41] into HCGHCRAMYAPPIA [SEQ ID NO: 42], more typically into HCGxCRAMYAPPIA, wherein x is not Cys or His [SEQ ID NO: 43].

The present invention further relates to peptides with the modified redox motif comprising MHC class II T cell epitopes of soluble allofactors such as used in replacement therapies. The present invention further relates to methods of treatment and prevention of immune reactions against soluble allofactors. Examples of soluble allofactors are disclosed in WO2009101206.

As an example of the present invention the peptide of complementarity-determining region (CDR) 3 of the VH region of the B02C11 antibody, against factor VIII, CHG-CYCAVPDDPDA [SEQ ID NO: 44], is modified into HCH- GCYCAVPDDPDA [SEQ ID NO: 45], more typically into HCxGCYCAVPDDPDA, wherein x is not Cys or His [SEQ ID NO: 46].

As a further example the peptide derived from another anti-Factor VIII antibody, CGHCGGIRLHPTHYSIR [SEQ ID NO: 47] is modified into HCGHCGGIRLHPTHYSIR [SEQ ID NO: 48], more typically into HCGxCG-GIRLHPTHYSIR wherein x is not Cys or His [SEQ ID NO: 49].

The present invention further relates to peptides with the modified redox motif comprising MHC class II T cell epitopes of tumour associated antigens. The present invention further relates to methods of treatment and prevention of tumours. Examples of relevant tumours (e.g. oncogene, proto-oncogene, viral protein, a surviving factor, clonotypic determinant) and tumour associated antigens are disclosed in WO WO2009101205. Such tumor associated antigens include viral antigens of tumour causing viruses such as HPV, tumour associated antigens of a patient which have a wild-type sequence but have an increased expression in tumours, or antigens which have a mutated sequence by point mutations, deletions, frame shifts, or chromosomal rearrangements.

As an example of the teaching of the present invention the MAGE-3 peptide CHGCYRQVPGSDP [SEQ ID NO: 50] is modified into HCHGCYRQVPGSDP [SEQ ID NO: 51], more typical into HCxGCYRQVPGSDP wherein x is not Cys or His [SEQ ID NO: 52].

As a further example the cyclin D peptide CHGCFVAL-CATDV [SEQ ID NO: 53] is modified into HCHGCFVAL-CATDV [SEQ ID NO: 54], more typical into HCxGCFVAL-CATDV, wherein X is not Cys or His [SEQ ID NO: 55].

As a further example the surviving peptide CHGCFKELEGWEP [SEQ ID NO: 56] is modified into HCHGCFKELEGWEP [SEQ ID NO: 57], more typical into HCxGCFKELEGWEP wherein X is not Cys or His [SEQ ID NO: 58].

As a further example the Epstein Barr virus peptide CHGCVASSYAAAQ [SEQ ID NO: 59] is modified into HCHGCVASSYAAAQ [SEQ ID NO: 60], more typical into HCxGCVASSYAAAQ wherein X is not Cys or His [SEQ ID NO: 61].

The present invention further relates to peptides with the modified redox motif comprising MHC class II T cell epitopes of alloantigenic protein of an allograft. The present invention further relates to methods of treatment and prevention of allograft rejection. Examples are bone marrow grafts, solid organ grafts such as kidney, lung, heart, liver, pancreas, bone or skin, or cellular grafts such as cord blood cell graft, stem cell graft, or pancreatic islet cell grafts. Examples of alloantigenic proteins are disclosed in WO2009100505, such as minor histocompatibility antigens, major histocompatibility antigens or tissue-specific antigens.

As an example of the present invention, the peptide from murine Dby antigen CHGCFNSNRANSS [SEQ ID NO: 62] is modified into HCHGCFNSNRANSS [SEQ ID NO: 63], more particular into HCxGCFNSNRANSS wherein x is not Cys or His [SEQ ID NO: 64].

In another example the sequence from human Dby CGHCLVLAPTREL [SEQ ID NO: 65], is modified into HCGHCLVLAPTREL [SEQ ID NO: 66], more particularly into HCGxCLVLAPTREL, wherein x is not Cys or His [SEQ ID NO: 67].

In another example the murine Black 6 strain specific peptide CGHCPEFLEQKRA [SEQ ID NO: 68] is modified into HCGHCPEFLEQKRA [SEQ ID NO: 69], more typically into HCGxCPEFLEQKRA, wherein x is not Cys or His [SEQ ID NO: 70].

For all the above peptides additional variant are envisaged, wherein between histidine and cysteine, one or two amino acids X are present. Typically these external amino acid(s) X is (are) not His, Cys, Ser or Thr.

The peptides of the present invention can also be used in diagnostic in vitro methods for detecting class II restricted CD4+ T cells in a sample. In this method a sample is contacted with a complex of an MHC class II molecule and a peptide according to the present invention. The CD4+ T cells detected by measuring the binding of the complex with cells in the sample, wherein the binding of the complex to a cell is indicative for the presence of CD4+ T cells in the sample.

The complex can be a fusion protein of the peptide and an MHC class II molecule. Alternatively MHC molecules in the complex are tetramers. The complex can be provided as a soluble molecule or can be attached to a carrier.

The T cell epitope corresponding to an antigenic protein (or immunogen) suitable for use in the context of the present invention is typically a universal or promiscuous T cell epitope (i.e. a T cell epitope capable of binding to a majority of the MHC class II molecules), more particularly present upon an airborne allergen or a foodborne allergen. In particular embodiments, the allergen is selected from the group consisting of rhino-sinusitis allergens, allergic bronchial asthma allergens and atopic dermatitis allergens. Allergens can also be main allergens present in moulds or various drugs such as hormones, antibiotics, enzymes, etc. (See also the definition in *Clin. Exp. Allergy* 26, 494-516 (1996) and in Molecular Biology of Allergy and Immunology, Ed. R. Bush (1996)). Other allergens related to specific allergic diseases are also well known in the art and can be found on the internet, e.g. on www.allergome.org.

Autoimmune diseases are broadly classified into two categories, organ-specific and systemic diseases. The precise aetiology of systemic auto-immune diseases is not identified. In contrast, organ-specific auto-immune diseases are related to a specific immune response including B and T cells, which targets the organ and thereby induces and maintains a chronic state of local inflammation. Examples of organ-specific auto-immune diseases include type 1 diabetes, myasthenia gravis, thyroiditis and multiple sclerosis. In each of these conditions, a single or a small number of auto-antigens have been identified, including insulin, the acetylcholine muscle receptor, thyroid peroxidase and major basic protein, respectively. It is well recognised that suppression of this organ-specific immune response is beneficial and leads to partial or complete recovery of organ function. There is, however, no therapy, which would suppress such an immune response in an antigen-specific manner. Current therapy rather makes use of non-specific suppression obtained by the use of corticosteroids and immunosuppressive agents, all exhibiting significant side-effects related to their absence of specificity, thereby limiting their use and their overall efficacy. A non-limiting list of examples of organ specific autoimmune disorders and auto-antigens involved therein which are envisaged within the context of the present invention are:

thyroid diseases: thyroglobulin, thyroid peroxidase, TSH receptor type 1 diabetes: insulin (proinsulin), glutamic acid decarboxylase (GAD), tyrosine phosphatase IA-2, heat-shock protein HSP65, islet-specific glucose6-phosphatase catalytic subunit related protein (IGRP)

Adrenalitis: 21-OH hydroxylase
polyendocrine syndromes: 17-alpha hydroxylase, histidine decarboxylase, tryptophan hydroxylase, tyrosine hydroxylase
gastritis & pernicious anemia: H+/K+ ATPase intrinsic factor
multiple sclerosis: myelin oligodendrocyte glycoprotein (MOG), myelin basic protein (MBP), proteolipid (PLP)
myasthenia gravis: acetyl-choline receptor
ocular diseases: retinol-binding protein (RBP)
inner ear diseases: type II and type IX collagen
celiac disease: tissue transglutaminase
inflammatory bowel diseases: pANCA histone H1 protein
Atherosclerosis: heat-shock protein HSP60

According to the present invention, immunogenic peptides are provided which comprise a T-cell epitope of an antigen (self or non-self) with a potential to trigger an immune reaction. In a particular embodiment, the T-cell epitope is a dominant T-cell epitope. Accordingly, in particular embodiments, the methods of treatment and prevention of the present invention comprise the administration of an immunogenic peptide as described herein, wherein the peptide comprise a T-cell epitope of an antigenic protein which plays a role in the disease to be treated (for instance such as those described above). In further particular embodiments, the epitope used is a dominant epitope.

The present invention further relates to methods to produce peptides with a MHC class II T cell epitope and a modified redox motif.

In a first step the method comprises the step of providing the sequence of an antigenic protein of interest and identifying an MHC class II T cell epitope sequence in the antigen. Epitope sequences may have been described yet for the antigenic protein under consideration. Alternatively they are determined by in silico methods, in vitro methods or in vivo methods. In addition the antigenic protein is screened for the presence of the modified redox motif, which requires no specific in silico methods.

There is a very small, but existing, chance that an antigenic protein contains within its sequence a H-X(0,2)C-X(2)-[CST] [SEQ ID NO: 78, 90 or 91] or [CST]-X(2)-C-X(0,2)-H [SEQ ID NO: 79, 92 or 93] motif in the close proximity of a T cell epitope sequence (i.e. separated from the T cell epitope by 7 or less amino acids). If so, a fragment of the antigenic protein comprising T cell epitope and motif can be used for the methods and uses of the prevent invention. The epitope in such proteins may have been discussed in the prior art but the presence, let alone, the relevance of such modified redox motif is not discussed. There has been accordingly no incentive in the prior art to select such peptide fragments, or to use such peptide fragments for the methods described herein. In certain embodiments, wherein the peptide is based on a fragment of a protein which contains an MHC class II T cell epitope and a modified redox motif such a peptide sequence may be further modified by changing the length of the sequence between the epitope and the modified redox motif, changing amino acids in the linker sequence, changing a Ser or Thr in the motif into a cysteine or changing amino acids at one or both X positions within the motif.

Other antigenic proteins which are used for the design of peptides may contain a H-X(0,2)-C-X(2)-[CST] [SEQ ID NO: 78, 90 or 91] or [CST]-X(2)-C-X(0,2)-H [SEQ ID NO: 79, 92 or 93] sequence in its sequence which is further remote from a MHC class II T cell epitope (more than 7 amino acids from the epitope sequence).

In such cases a peptide can be produced wherein only the distance between the epitope and the motif is shortened and whereby the sequence of the motif and neighbouring amino acids are preserved. If deemed suitable, amino acids outside the motif, Serine or threonine in the motif or one or both X positions are changed.

More general, antigenic proteins which are used for the design of peptides will not contain a H-X(0,2)-C-X(2)-[CST] [SEQ ID NO: 78, 90 or 91] or [CST]-X(2)-C-X(0,2)-H [SEQ ID NO: 79, 92 or 93] sequence within their protein sequence. Peptides in accordance of the present invention will be prepared by synthesising a peptide wherein T cell epitope and modified redox motif will be separated by 0 to 7 amino acids. In certain embodiments the modified redox motif can be obtained by introducing 1, 2 or 3 mutations outside the epitope sequence, to preserve the sequence context as occurring in the protein. Typically amino-acids in P−2 and P−1, as well as in P+10 and P+11, with reference to the nonapeptide which are part of the natural sequence are preserved in the peptide sequence. These flanking residues generally stabilize the binding to MHC class II. In other embodiments the sequence N terminal or C terminal of the epitope will be unrelated to the sequence of the antigenic protein containing the T cell epitope sequence.

In other specific embodiments, peptides are prepared by modifying peptides with a T cell epitope and a C-X(2)-[CST] [SEQ ID NO: 77] or [CST]-X(2)-C [SEQ ID NO: 76] motif as disclosed in WO2008/017517. Addition of a histidine or modification of an amino acid into a histidine leads to peptides of the present invention with a H-X(2,0)-C-X(2)-[CST][SEQ ID NO: 78, 90 or 91] or [CST]-X(2)-C-X(0,2)-H [SEQ ID NO: 79, 92 or 93] sequence.

Thus based upon the above methods for designing a peptide, a peptide is generated by chemical peptide synthesis, recombinant expression methods or in more exceptional cases, proteolytic or chemical fragmentation of proteins.

Peptides as produced in the above methods can be tested for the presence of a T cell epitope in in vitro and in vivo methods, can be tested for their reducing activity in in vitro assays. As a final quality control, the peptides can be tested in in vitro assays to verify whether the peptides can generated CD4+ T cells which are cytolytic via an apoptotic pathway for antigen presenting cells presenting the antigen which contains the epitope sequence which is also present in the peptide with the modified redox motif.

The identification and selection of a T-cell epitope from antigenic proteins, for use in the context of the present invention is known to a person skilled in the art.

To identify an epitope suitable for use in the context of the present invention, isolated peptide sequences of an antigenic protein are tested by, for example, T cell biology techniques, to determine whether the peptide sequences elicit a T cell response. Those peptide sequences found to elicit a T cell response are defined as having T cell stimulating activity.

Human T cell stimulating activity can further be tested by culturing T cells obtained from an individual sensitive to e.g. a mite allergen, (i.e. an individual who has an lgE mediated immune response to a mite allergen) with a peptide/epitope derived from the allergen and determining whether proliferation of T cells occurs in response to the peptide/epitope as measured, e.g., by cellular uptake of tritiated thymidine. Stimulation indices for responses by T cells to peptides/epitopes can be calculated as the maximum CPM in response to a peptide/epitope divided by the control CPM. A T cell stimulation index (S.I.) equal to or greater than two times the background level is considered "positive." Positive results are used to calculate the mean stimulation index for each peptide/epitope for the group of peptides/epitopes tested.

Non-natural (or modified) T-cell epitopes can further optionally be tested on their binding affinity to MHC class II molecules. This can be performed in different ways. For instance, soluble HLA class II molecules are obtained by lysis of cells homozygous for a given class II molecule. The latter is purified by affinity chromatography. Soluble class II molecules are incubated with a biotin-labelled reference peptide produced according to its strong binding affinity for that class II molecule. Peptides to be assessed for class II binding are then incubated at different concentrations and their capacity to displace the reference peptide from its class II binding is calculated by addition of neutravidin. Methods can be found in for instance Texier et al., (2000) *J. Immunology* 164, 3177-3184.)

According to the present invention, the immunogenic properties of T cell epitopes are increased by linking it to the modified redox motif which has enhance reducing properties. Particularly, peptides of the present invention comprising at least one T cell epitope and the modified redox motif as described herein have a mean T cell stimulation index of greater than or equal to 2.0. A peptide having a T cell stimulation index of greater than or equal to 2.0 is considered useful as a therapeutic agent. More particularly, peptides according to the invention have a mean T cell stimulation index of at least 2.5, at least 3.5, at least 4.0, or even at least 5.0. In addition, peptides have typically a positivity index (P.I.) of at least about 100, at least 150, at least about 200 or at least about 250. The positivity index for a peptide is determined by multiplying the mean T cell stimulation index by the percent of individuals, in a population of individuals with an immune response (e.g., sensitive to house dust mite) (e. g., at least 9 individuals, at least 16 individuals or at least 29 or 30, or even more), who have T cells that respond to the peptide (thus corresponding to the SI multiplied by the promiscuous nature of the peptide/epitope). Thus, the positivity index represents both the strength of a T cell response to a peptide (S.I.) and the frequency of a T cell response to a peptide in a population of individuals with an immune response (e.g.) sensitive to house dust mite. In order to determine optimal T cell epitopes by, for example, fine mapping techniques, a peptide having T cell stimulating activity and thus comprising at least one T cell epitope as determined by T cell biology techniques is modified by addition or deletion of amino acid residues at either the amino- or carboxyterminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. T cell epitopes or peptides are selected based on various factors, including the strength of the T cell response to the peptide/epitope (e.g., stimulation index) and the frequency of the T cell response to the peptide in a population of individuals.

Additionally and/or alternatively, one or more in vitro algorithms can be used to identify a T cell epitope sequence within an antigenic protein. Suitable algorithms include, but are not limited to those described in Zhang et al. (2005) *Nucleic Acids Res* 33, W180-W183 (PREDBALB); Salomon & Flower (2006) *BMC Bioinformatics* 7, 501 (MHCBN); Schuler et al. (2007) *Methods Mol. Biol.* 409, 75-93 (SYFPEITHI); Donnes & Kohlbacher (2006) *Nucleic Acids Res.* 34, W194-W197 (SVMHC); Kolaskar & Tongaonkar (1990) *FEBS Lett.* 276, 172-174, Guan et al. (2003) *Appl. Bioinformatics* 2, 63-66 (MHCPred) and Singh and Raghava (2001) *Bioinformatics* 17, 1236-1237 (Propred).

More particularly, such algorithms allow the prediction within an antigenic protein of one or more octa- or nona-peptide sequences which will fit into the groove of an MHC II molecule and this for different HLA types.

The peptides of the present invention can be generated using recombinant DNA techniques, in bacteria, yeast, insect cells, plant cells or mammalian cells. In view of the limited length of the peptides, they can be prepared by chemical peptide synthesis, wherein peptides are prepared by coupling the different amino acids to each other.

Chemical synthesis is particularly suitable for the inclusion of e.g. D-amino acids, amino acids with non-naturally occurring side chains or natural amino acids with modified side chains such as methylated cysteine.

Chemical peptide synthesis methods are well described and peptides can be ordered from companies such as Applied Biosystems and other companies.

Peptide synthesis can be performed as either solid phase peptide synthesis (SPPS) or contrary to solution phase peptide synthesis. The best-known SPPS methods are t-Boc and Fmoc solid phase chemistry: During peptide synthesis several protecting groups are used. For example hydroxyl and carboxyl functionalities are protected by t-butyl group, lysine and tryptophan are protected by t-Boc group, and asparagine, glutamine, cysteine and histidine are protected by trityl group, and arginine is protected by the pbf group. If appropriate, such protecting groups can be left on the peptide after synthesis. Peptides can be linked to each other to form longer peptides using a ligation strategy (chemoselective coupling of two unprotected peptide fragments) as originally described by Kent (Schnelzer & Kent (1992) *Int. J. Pept. Protein Res.* 40, 180-193) and reviewed for example in Tam et al. (2001) *Biopolymers* 60, 194-205 provides the tremendous potential to achieve protein synthesis which is beyond the scope of SPPS. Many proteins with the size of 100-300 residues have been synthesised successfully by this method. Synthetic peptides have continued to play an ever increasing crucial role in the research fields of biochemistry, pharmacology, neurobiology, enzymology and molecular biology because of the enormous advances in the SPPS.

Alternatively, the peptides can be synthesised by using nucleic acid molecules which encode the peptides of this invention in an appropriate expression vector which include the encoding nucleotide sequences. Such DNA molecules may be readily prepared using an automated DNA synthesiser and the well-known codon-amino acid relationship of the genetic code. Such a DNA molecule also may be obtained as genomic DNA or as cDNA using oligonucleotide probes and conventional hybridisation methodologies. Such DNA molecules may be incorporated into expression vectors, including plasmids, which are adapted for the expression of the DNA and production of the polypeptide in a suitable host such as bacterium, e.g. *Escherichia coli*, yeast cell, animal cell or plant cell.

The physical and chemical properties of a peptide of interest (e.g. solubility, stability) are examined to determine whether the peptide is/would be suitable for use in therapeutic compositions. Typically this is optimised by adjusting the sequence of the peptide. Optionally, the peptide can be modified after synthesis (chemical modifications e.g. adding/deleting functional groups) using techniques known in the art.

T cell epitopes on their own are thought to trigger early events at the level of the T helper cell by binding to an appropriate HLA molecule on the surface of an antigen presenting cell and stimulating the relevant T cell subpopulation. These events lead to T cell proliferation, lymphokine secretion, local inflammatory reactions, the recruitment of additional immune cells to the site, and activation of the B cell cascade leading to production of antibodies. One isotype of these antibodies, lgE, is fundamentally important in the development of allergic symptoms and its production is influenced early in the cascade of events, at the level of the T helper cell, by the nature of the lymphokines secreted. A T cell epitope is the basic element or smallest unit of recognition by a T cell receptor where the epitope comprises amino acid residues essential to receptor recognition, which are contiguous in the amino acid sequence of the protein.

However, upon administration of the peptides with a T-cell epitope and a redox motif, the following events are believed to happen:

- activation of antigen (i) specific T cells resulting from cognate interaction with the antigen-derived peptide presented by MHC-class II molecules;
- the reductase sequence reduces T cell surface proteins, such as the CD4 molecule. the second domain of which contains a constrained disulfide bridge. This transduces a signal into T cells. Among a series of consequences related to increased oxidative pathway, important events are increased calcium influx and translocation of the NF-kB transcription factor to the nucleus. The latter results in increased transcription of IFN-gamma and granzymes, which allows cells to acquire cytolytic properties via an apoptosis-inducing mechanism; the cytolytic property affects cells presenting the peptide by a mechanism, which involves granzyme B secretion, and Fas-FasL interactions. Since the cell killing effect is obtained via an apoptotic pathway, cytolic cells is a more appropriate term for these cells than cytotoxic cells. Destruction of the antigen-presenting target cells prevents activation of other T cells specific for epitopes located on the same antigen, or to an unrelated antigen that would be processed by the same antigen-presenting cell; an additional consequence of T cell activation is to suppress activation of bystander T cells by a cell-cell contact dependent mechanism. In such a case, T cells activated by an antigen presented by a different antigen-presenting cell is also suppressed provided both cytolytic and bystander T cells are in close proximity, namely activated on the surface of the same antigen-presenting cell.

The above-postulated mechanism of action is substantiated with experimental data disclosed in the above cited PCT application and publications of the present inventor. The present invention provides methods for generating antigen-specific cytolytic CD4+ T cells either in vivo or in vitro and, independently thereof, methods to discriminate cytolytic CD4+ T cells from other cell populations such as Foxp3+ Tregs based on characteristic expression data.

The present invention describes in vivo methods for the production of the antigen-specific CD4+ T cells. A particular embodiment relates to the method for producing or isolating the CD4+ T cells by immunising animals (including humans) with the peptides of the invention as described herein and then isolating the CD4+ T cells from the immunised animals. The present invention describes in vitro methods for the production of antigen specific cytolytic CD4+ T cells towards APC. The present invention provides methods for generating antigen specific cytolytic CD4+ T cells towards APC.

In one embodiment, methods are provided which comprise the isolation of peripheral blood cells, the stimulation of the cell population in vitro by an immunogenic peptide according to the invention and the expansion of the stimulated cell population, more particularly in the presence of IL-2. The methods according to the invention have the advantage a high number of CD4+ T cells is produced and that the CD4+ T cells can be generated which are specific for the antigenic protein (by using a peptide comprising an antigen-specific epitope).

In an alternative embodiment, the CD4+ T cells can be generated in vivo, i.e. by the injection of the immunogenic peptides described herein to a subject, and collection of the cytolytic CD4+ T cells generated in vivo.

The antigen-specific cytolytic CD4+ T cells towards APC, obtainable by the methods of the present invention are of particular interest for the administration to mammals for immunotherapy, in the prevention of allergic reactions and the treatment of auto-immune diseases. Both the use of allogenic and autogeneic cells are envisaged.

Cytolytic CD4+ T cells populations are obtained as described herein below.

Antigen-specific cytolytic CD4+ T cells as described herein can be used as a medicament, more particularly for use in adoptive cell therapy, more particularly in the treatment of acute allergic reactions and relapses of autoimmune diseases such as multiple sclerosis. Isolated cytolytic CD4+ T cells or cell populations, more particularly antigen-specific cytolytic CD4+ T cell populations generated as described are used for the manufacture of a medicament for the prevention or treatment of immune disorders. Methods of treatment by using the isolated or generated cytolytic CD4+ T cells are disclosed.

As explained in WO2008/017517 cytolytic CD4+ T cells towards APC can be distinguished from natural Treg cells based on expression characteristics of the cells. More particularly, a cytolytic CD4+ T cell population demonstrates one or more of the following characteristics compared to a natural Treg cell population:

- an increased expression of surface markers including CD103, CTLA-4, Fasl and ICOS upon activation,
- intermediate expression of CD25,
- expression of CD4, ICOS, CTLA-4, GITR and low or no expression of CD127 (IL7-R), no expression of CD27.
- expression of transcription factor T-bet and egr-2 (Krox-20) but not of the transcription repressor Foxp3,
- a high production of IFN-gamma and no or only trace amounts of IL-10, IL-4, IL-5, IL-13 or TGF-beta.

Further the cytolytic T cells express CD45RO and/or CD45RA, do not express CCR7, CD27 and present high levels of granzyme B and other granzymes as well as Fas ligand. The peptides of the invention will, upon administration to a living animal, typically a human being, elicit specific T cells exerting a suppressive activity on bystander T cells. This mechanism also implies and the experimental results show that the peptides of the invention, although comprising a specific T-cell epitope of a certain antigen, can be used for the prevention or treatment of disorders elicited by an immune reaction against other T-cell epitopes of the same antigen or in certain circumstances even for the treatment of disorders elicited by an immune reaction against other T-cell epitopes of other different antigens if they would be presented through the same mechanism by MHC class II molecules in the vicinity of T cells activated by peptides of the invention.

Isolated cell populations of the cell type having the characteristics described above, which, in addition are antigen-specific, i.e. capable of suppressing an antigen-specific immune response are disclosed.

The peptides of the invention may also be used in gene therapy methods well known in the art and the terminology used herein explaining the use of peptides according to the invention also includes the use of nucleic acids encoding or expressing immunogenic peptides according to the invention.

The present invention describes nucleic acid sequences encoding the peptides of the present invention and methods for their use. Different methods of achieving, by way of gene therapy, levels of peptides, homologues or derivatives thereof according to the invention in a mammal in vivo are envisaged within the context of the present invention. Recombinant nucleic acid molecules encoding protein sequences can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognised by the cells normal mechanisms for transcription and translation, and a gene product will be expressed. Other methods have also been attempted for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilising endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery into vascular cells. As used herein, "gene transfer" means the process of introducing a foreign nucleic acid molecule into a cell, which is commonly performed to enable the expression of a particular product encoded by the gene. The product may include a protein, polypeptide, anti-sense DNA or RNA, or enzymatically active RNA. Gene transfer can be performed in cultured cells or by direct administration into mammals. In another embodiment, a vector comprising a nucleic acid molecule sequence encoding a peptide according to the invention is provided. In particular embodiments, the vector is generated such that the nucleic acid molecule sequence is expressed only in a specific tissue. Methods of achieving tissue-specific gene expression are well known in the art. This can be for example achieved by placing the sequence encoding a peptide according to the invention under control of a promoter which directs expression in one or more particular tissues.

Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding peptides, homologues or derivatives thereof according to the invention into the targeted tissues or cell population. Methods which are well known to those skilled in the art can be used to construct recombinant viral vectors containing such coding sequences.

Accordingly, the present invention discloses the use of a nucleic acid which is capable of expressing the peptides of the invention, in vivo, for the treatment and/or prevention of diseases driven by an immune response to a foreign or self antigen. According to one embodiment, the nucleic acid capable of expressing a peptide according to the invention in vivo is a sequence encoding such a peptide, which is operably linked to a promoter. Such a sequence can be administered directly or indirectly. For instance, an expression vector containing the coding sequence for a peptide according to the invention may be inserted into cells, after which the cells are grown in vitro and then injected or infused into the patient. Alternatively the nucleic acid capable of expressing a peptide according to the invention in vivo is a sequence which modifies endogenous expression of the cells. The gene therapy method may involve the use of an adenovirus vector including a nucleotide sequence coding for peptides, homologues or derivatives thereof according to the invention or a naked nucleic acid molecule coding for a peptide according to the invention. Alternatively, engineered cells containing a nucleic acid molecule coding for a peptide according to the invention may be injected.

Where the administration of one or more peptides according to the invention is ensured through gene transfer (i.e. the administration of a nucleic acid which ensures expression of peptides according to the invention in vivo upon administration), the appropriate dosage of the nucleic acid can be determined based on the amount of peptide expressed as a result of the nucleic acid, such as e.g. by determining the concentration of peptide in the blood after administration. Thus, in a particular embodiment, the peptides of the invention are administered through the use of polynucleotides encoding the peptides, whether in an expression vector or not and thus the present invention also relates to gene therapy methods. Another particular embodiment relates to the use of methods to induce a local overexpression of the peptides of the invention for the treatment or prevention of immune disorders.

The present invention provides pharmaceutical compositions comprising one or more peptides according to the present invention, further comprising a pharmaceutically acceptable carrier. As detailed above, the present invention also relates to the compositions for use as a medicine or to methods of treating a mammal of an immune disorder by using the composition and to the use of the compositions for the manufacture of a medicament for the prevention or treatment of immune disorders. The pharmaceutical composition could for example be a vaccine suitable for treating or preventing immune disorders, especially airborne and foodborne allergy, as well as diseases of allergic origin. As an example described further herein of a pharmaceutical composition, a peptide according to the invention is adsorbed on an adjuvant suitable for administration to mammals, such as aluminium hydroxide (alum). Typically, 50 µg of the peptide adsorbed on alum are injected by the subcutaneous route on 3 occasions at an interval of 2 weeks. It should be obvious for those skilled in the art that other routes of administration are possible, including oral, intranasal or intramuscular. Also, the number of injections and the amount injected can vary depending on the conditions to be treated. Further, other adjuvants than alum can be used, provided they facilitate peptide presentation in MHC-class II presentation and T cell activation. Thus, while it is possible for the active ingredients to be administered alone, they typically are presented as pharmaceutical formulations. The formulations, both for veterinary and for human use, of the present invention comprise at least one active ingredient, as above described, together with one or more pharmaceutically acceptable carriers. The present invention relates to pharmaceutical compositions, comprising, as an active ingredient, one or more peptides according to the invention, in admixture with a pharmaceutically acceptable carrier. The pharmaceutical composition of the present invention should comprise a therapeutically effective amount of the active ingredient, such as indicated hereinafter in respect to the method of treatment or prevention. Optionally, the composition further comprises other therapeutic ingredients. Suitable other therapeutic ingredients, as well as their usual dosage depending on the class to which they belong, are well known to those skilled in the art and can be selected from other known drugs used to treat immune disorders.

The term "pharmaceutically acceptable carrier" as used herein means any material or substance with which the active ingredient is formulated in order to facilitate its application or dissemination to the locus to be treated, for instance by dissolving, dispersing or diffusing the composition, and/or to facilitate its storage, transport or handling without impairing its effectiveness. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the immunogenic peptide in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in the pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 µm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids (C10-C22), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives typically contain 8 to 22 carbon atoms. Examples of alkylarylsulphonates are the sodium, calcium or alcanolamine salts of dodecyl benzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidyl-ethanolamine, phosphatidylserine, phosphatidylglycerine, lysolecithin, cardio-lipin, dioctanylphosphatidylcholine, dipalmitoylphoshatidylcholine and their mixtures.

Suitable non-ionic surfactants include polyethoxylated and poly-propoxylated derivatives of alkyl phenols, fatty alcohols, fatty acids, aliphatic amines or amides containing at least 12 carbon atoms in the molecule, alkylarene sulphonates and dialkylsulphosuccinates, such as polyglycol ether derivatives of aliphatic and cycloaliphatic alcohols, saturated and unsaturated fatty acids and alkylphenols, the derivatives typically containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants. Suitable cationic surfactants include quatemary ammonium salts, particularly halides, having 4 hydrocarbon radicals optionally substituted with halo, phenyl, substituted phenyl or hydroxy; for instance quatemary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, New Jersey, 1981), "Tensid-Taschenbucw', 2 d ed. (Hanser Verlag, Vienna, 1981) and "Encyclopaedia of Surfactants, (Chemical Publishing Co., New York, 1981). Peptides, homologues or derivatives thereof according to the invention (and their physiologically acceptable salts or pharmaceutical compositions all included in the term "active ingredients") may be administered by any route appropriate to the condition to be treated and appropriate for the compounds, here the proteins and fragments to be administered. Possible routes include regional, systemic, oral (solid form or inhalation), rectal, nasal, topical (including ocular, buccal and sublingual), vaginal and parenteral (including subcutaneous, intramuscular, intravenous, intradermal, intra-arterial, intrathecal and epidural). The preferred route of administration may vary with for example the condition of the recipient or with the diseases to be treated. As described herein, the carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intraarterial, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product. Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For local treatments for example on the skin, such as of the joint, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), particularly 0.2 to 15% w/w and more particularly 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogues. The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabiliser, typically by including both an oil and a fat. Together, the emulsifier(s) with or without stabiliser(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, and particularly butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used. Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavoured basis, usually sucrose and acacia or tragacanth; pastilles comprising the active ingredient in an inert basis such as gelatin and glycerine, or sucrose and acacia; and mouthwashes comprising the active ingredient in a suitable liquid carrier. Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc.), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents. Formulations suitable for vaginal administration may be presented as pessaries, tampons, creams, gels, pastes, foams or spray formulations containing in addition to the active ingredient such carriers as are known in the art to be appropriate. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Typical unit dosage formulations are those containing a daily dose or unit daily sub-dose, as herein above recited, or an appropriate fraction thereof, of an active ingredient. It should be understood that in addition to the ingredients particularly mentioned above the formulations of this invention may include other agents conventional in the art having regard to the type of formulation in question, for example those suitable for oral administration may include flavouring agents. Peptides, homologues or derivatives thereof according to the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods. Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polyniethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injection include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Cytolytic CD4+ T cells as obtained in the present invention, induce APC apoptosis after MHC-class II dependent cognate activation, affecting both dendritic and B cells, as demonstrated in vitro and in vivo, and (2) suppress bystander T cells by a contact-dependent mechanism in the absence of IL-10 and/or TGF-beta. Cytolytic CD4+ T cells can be distinguished from both natural and adaptive Tregs, as discussed in detail in WO2008/017517.

The present invention will now be illustrated by means of the following examples which are provided without any limiting intention. Furthermore, all references described herein are explicitly included herein by reference.

EXAMPLES

Example 1: Methodology to Assess Reducing Activity of Peptides

The reductase activity of the peptides is determined using a fluorescent described in Tomazzolli et al. (2006) *Anal. Biochem.* 350, 105-112. Two peptides with a FITC label become self-quenching when they covalently attached to each other via a disulfide bridge. Upon reduction by a peptide in accordance with the present invention, the reduced individual peptides become fluorescent again.

Control experiments were performed with a peptide with a "normal" reducing peptide, i.e. a peptide with a redox motif but without additional histidine and with a peptide comprising no redox motif.

Example 2: Determination of the Activation of Cells

Antigen specific cytolytic cells as obtained by the peptides of the present invention are capable to drive antigen presenting cells into apoptosis. To evaluate the activation and prevent eventual over-activation of the cytolytic cells which would drive them themselves in apoptosis, the phosphorylation status of Akt and Shp allows to draw a correlation between activation of a cell (capable of apoptosis) and over-activation of a cell (self-apoptosis).

Example 3: Design of MOG Derived Peptides

An example of the peptides of the present invention is the peptide with sequence HCPYCSRVVHLYRNGKD [SEQ ID NO: 1]. This peptide comprises the SRVVHLYRNGKD [SEQ ID NO: 2] fragment of the human MOG protein (Myelin Oligodendrocyte Glycoprotein)(uniprot Q16653 accession number], which itself contains the VVHLYRNGK nonapeptide MHC class II T cell epitope sequence [SEQ ID NO: 3].

According to the definitions mentioned in the application, this 17 AA peptide comprises:
- a modified redox motif H-C-X(2)-C [SEQ ID NO: 80], with Pro and Tyr as x,
- a linker of 2 amino acids (Ser, Arg) between the motif and the T cell epitope sequence,
- a MHC class T cell epitope of nine amino acids with sequence VVHLYRNGK [SEQ ID NO: 3],
- a one amino acid flanking sequence (Asp) c terminal of the epitope.

Compared to the sequence of the MOG peptide fragment YRPPFSRVVHLYRNGKD [SEQ ID NO: 4], YRPPF [SEQ ID NO: 5] in the sequence has been replace by the sequence HCPYC [SEQ ID NO: 6].

Control peptides are:
YRPPFSRVVHLYRNGKD [SEQ ID NO: 4], i.e. the above fragment of MOG.
CPYCSRVVHLYRNGKD [SEQ ID NO: 7], with a C(X)2C motif [SEQ ID NO: 71] but lacking the additional histidine.

SRVVHLYRNGKD [SEQ ID NO: 2], lacking the also the C(X)2C motif [SEQ ID NO: 71].

Peptides have been prepared by peptide synthesis with a $CONH_2$ modified carboxyterminus and are tested for purity by mass spectrometry and HPLC.

Example 4: In Vitro Expansion of Cell Lines

Figure 1:
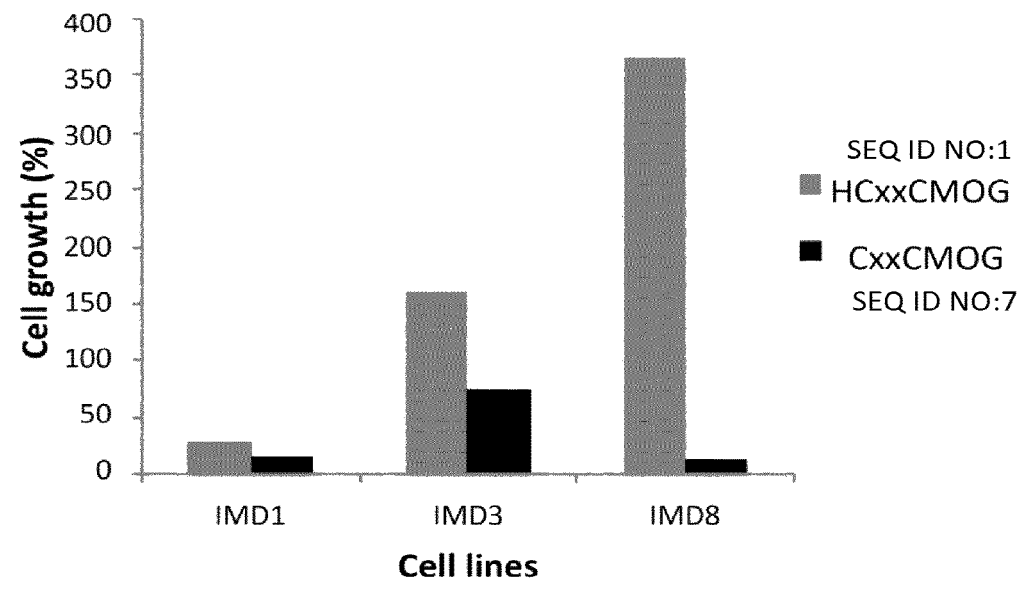

Response of naive human CD4+ T cell lines towards peptides with a T cell epitope of MOG and a redox motif without (right bars FIG. 1) [SEQ ID NO: 7] and with additional histidine (left bars FIG. 1) [SEQ ID NO: 1].

Equal amounts of both peptides were added to different naïve human CD4+ T cell lines. The results represent cell number (as % of initial cell seeded) at the end of a clinical scale process leading to the production of differentiated T cells with cytolytic properties.

This significant increase of cell conversion in vitro is thus obtained when the added histidine is added, but only for cell lines of persons presenting the DR2 haplotype, and not for others haplotypes.

The use of such peptides is thus particularly interesting for the DR2+ population (again 70% of the MS population) it seems that there is a definite (and unexpected) advantage of using his-containing peptides.

Example 5: Use of a T Cell Epitope of MOG Protein in an In Vivo Model for Multiple Sclerosis Multiple sclerosis can be induced in experimental models by immunisation with the Myelin Oligodendrocyte Glycoprotein (MOG) peptide with a T cell epitope.

A group of C57BL/6 mice is adoptively transferred with a CD4+ MOG-specific effector T cell clone following a protocol meant to induce a multiple sclerosis-like syndrome. This involves administration of the MOG peptide in complete Freund's adjuvant and 2 injections of Pertussis toxin. This protocol elicits an expansion of the effector T cell clone, which results in the development of signs compatible with multiple sclerosis within 12 days after the MOG peptide administration. A second group of C57BL/6 mice is first adoptively transferred with a MOG-specific cytolytic T cell clone (obtained using the peptide with [SEQ ID NO: 1]), followed after 1 day by the full protocol of disease induction.

Peptides with SEQ ID NO: 2, 4 and 7 are used as controls.

Example 6: Prevention and Suppression of Multiple Sclerosis

Groups of C57BL/6 mice are immunised subcutaneously (20 μg) with the peptide of example 1 which contains the modified sequence motif [SEQ ID NO: 1] or control peptide [SEQ ID NO: 2, 4 or 7] adsorbed onto aluminium hydroxide. Three injections are performed at 2-week intervals. Ten days after the last immunisation, mice are sacrificed and CD4+ T cells ($2\times10^6$ cells) are prepared from the spleen using magnetic beads. CD4+ T cells are then stimulated in vitro by the MOG T cell epitope (20 μg/ml) presented by adherent spleen cells ($2\times10^6$ cells).

After four re-stimulations, a T cell line is tested in a bystander suppression assay with, as target cells, polyclonal $CD4^+CD25^-$ cells obtained from animals in which EAE (Experimental autoimmune encephalomyelitis) is effective. Only the cells obtained from animals immunised with the peptide with SEQ ID NO: 1 and 7 containing the HC(X)2C [SEQ ID NO: 80] or C(X)2C [SEQ ID NO: 71] sequence motif have the capacity to induce death in target cells, as compared to the control consisting in effector $CD4+CD25^-$ from EAE animals.

A group of C57BL/6 mice is adoptively transferred with a CD4+ MOG-specific CD4+ T cell clone followed after 1 day by a protocol meant to induce a multiple sclerosis-like syndrome. This involves administration of the MOG peptide in complete Freund's adjuvant and 2 injections of Pertussis toxin. This protocol elicits an expansion of the effector T cell clone, which results in the development of signs compatible with multiple sclerosis within 12 days after the MOG peptide administration. The clinical score developed by mice pre-treated with a cytolytic T cell clone is compared to mice receiving only the full protocol of disease induction.

Example 7: Prevention of Multiple Sclerosis by Peptide Immunisation

In the model group, C57BL6 mice received, at day 0, SC injection of 100 μg MOG peptide/400 μg *Mycobacterium butyricum* in CFA and ip injection of 300 ng Bortetella pertussis in NaCl. At day +2, a second injection of *B. pertussis* is given.

In the prevention group, C57BL/6 mice are immunised by 5 injections with 20 μg of the peptide with SEQ ID NO: 1, which contains the sequence motif HC(X)2C [SEQ ID NO: 80], in IFA at 14 days interval before disease induction as in the model group. Control experiments are performed with the peptides with SEQ ID NO: 2, 4 and 7.

Scores are established as 0: no disease, 1: limp tail, 2: limp tail and loss of weight higher than 10%, 3: partial paralysis of hind limbs.

Example 9

Evaluation of Reductase Activity on a Synthetic Peptide

A FITC -NH-Gly-Cys-Asp-COOH peptide was synthesized (Eurogentec, Belgium) and self-quenched by solubilization in DMSO ((FITC-Gly-Cys-Asp)ox). The reduction of 2.5 μM (FITC-Gly-Cys-Asp)ox was followed on a 96 well plate during 40 minutes (25° C.) after incubation in PBS with peptide (25 μM) as listed in the accompanying table, or with 2 mM Dithiothreitol (DTT). Reduction was measured as a function of increase in fluorescence read at 530 nm after excitation at 494 nm, using a CytoFluor® multiplate reader (Applied Biosystems). Results are shown in the table of example 10 under the heading "Reductase activity".

Example 10

Polymerization of Human Recombinant CD4

Human recombinant CD4 (300 ng) is incubated in Hepes buffer with 50 μM of a peptide as listed in the Table for 15 minutes at 68° C. Fifty μM of DTT is used as a positive control under the same conditions. LDS sample buffer (7.5 μl; non-reducing) is then added to 15 μl of the peptide/CD4 mixture. The mixture is then submitted to non-reducing PAGE. After Coomassie Blue staining, protein bands are analyzed for the presence of monomeric, dimeric or multimeric recCD4, as identified by the decreased migratory capacities into the gel. The Table indicates whether or not a polymerization had occurred (+).

| Seq id no: | N-term | motif | linker epitope | C-term | Reductase activity (%) | CD4 polymerisation |
|---|---|---|---|---|---|---|
| 108 | H | CPYC | VRSLQP LALEGSLQK | RG | 68 | + |
| 109 | HAA | CPYC | VRSLQP LALEGSLQK | RG | 0 | + |
| 110 | AHA | CPYC | VRSLQP LALEGSLQK | RG | 13 | + |
| 111 | AAA | CPYC | VRSLQP LALEGSLQK | RG | 6 | + |
| 112 | AAA | CHPC | VRSLQP LALEGSLQK | RG | 75 | + |
| 113 | AAH | CHPC | VRSLQP LALEGSLQK | RG | 64 | + |
| 114 | AAA | CHGC | VRSLQP LALEGSLQK | RG | 22 | low |

The Table provides various combinations of amino acid sequences added at the amino-terminal end of a class II-restricted epitope of human proinsulin. These sequences are constituted of a amino-terminal sequence (N-term) in front of the first cysteine of the thioreductase-containing motif, the motif itself, a linker, the epitope and the C-terminal end (C-term). Reductase activity is expressed in % as described in Example 1. The polymerization of human recombinant CD4 is measured according to Example 2.

Peptides Disclosed in the Application.

In the below sequences 1-70, wherein x occurs, x is not cysteine or is not histidine.

Overview of disclosed peptide sequences.

[SEQ ID NO: 1]
HCPYCSRVVHLYRNGKD

[SEQ ID NO: 2]
SRVVELYRNGKD

[SEQ ID NO: 3]
VVHLYRNGK

[SEQ ID NO: 4]
YRPPFSRVVHLYRNGKD

[SEQ ID NO: 5]
YRPPF

[SEQ ID NO: 6]
HCPYC

[SEQ ID NO: 7]
CPYCSRVVHLYRNGKD

[SEQ ID NO: 8]
HCPYCSRVVHLYRNGK

[SEQ ID NO: 9]
CGFSSNYCQIYPPNANKIR

[SEQ ID NO: 10]
HCGFSSNYCQIYPPNANKIR

[SEQ ID NO: 11]
HCGFCSNYCQIYPPNANKIR

[SEQ ID NO: 12]
CHGSEPCIIHRGKPF

[SEQ ID NO: 13]
HCHGSEPCIIHRGKPF

[SEQ ID NO: 14]
HCHGCEPCIIHRGKPF

[SEQ ID NO: 15]
HCxGSEPCIIHRGKPF

[SEQ ID NO: 16]
HCxGCEPCIIHRGKPF

[SEQ ID NO: 17]
CHGCAQKKIIAEK

[SEQ ID NO: 18]
HCHGCAQKKIIAEK

[SEQ ID NO: 19]
HCxGCAQKKIIAEK

[SEQ ID NO: 20]
CGPCMNEELTERL

[SEQ ID NO: 21]
HCGPCMNEELTERL

[SEQ ID NO: 22]
CGPSAALTWVQTH

[SEQ ID NO: 23]
HCGPSAALTWVQTH

[SEQ ID NO: 24]
CHGCPTLLYVLFEV

[SEQ ID NO: 25]
HCHGCPTLLYVLFEV

[SEQ ID NO: 26]
HCxGCPTLLYVLFEV

[SEQ ID NO: 27]
CGPCGGYVPFHIQVP

[SEQ ID NO: 28]
HCGPCGGYVPFHIQVP

[SEQ ID NO: 29]
CGHCDKHIEQYLK

[SEQ ID NO: 30]
HCGHCDKHIEQYLK

[SEQ ID NO: 31]
HCGxCDKHIEQYLK

[SEQ ID NO: 32]
CGHCEKKICKMEK

[SEQ ID NO: 33]
HCGHCEKKICKMEK

[SEQ ID NO: 34]
HCGxCEKKICKMEK

-continued

CGHCKYVKQNTLK [SEQ ID NO: 35]

HCGHCKYVKQNTLK [SEQ ID NO: 36]

HCGxCKYVKQNTLK [SEQ ID NO: 37]

CGHCEHPIVVSGS [SEQ ID NO: 38]

HCGHCEHPIVVSGS [SEQ ID NO: 39]

HCGxCEHPIVVSGS [SEQ ID NO: 40]

CGHCRAMYAPPIA [SEQ ID NO: 41]

HCGHCRAMYAPPIA [SEQ ID NO: 42]

HCGxCRAMYAPPIA [SEQ ID NO: 43]

CHGCYCAVPDDPDA [SEQ ID NO: 44]

HCHGCYCAVPDDPDA [SEQ ID NO: 45]

HCxGCYCAVPDDPDA [SEQ ID NO: 46]

CGHCGGIRLHPTHYSIR [SEQ ID NO: 47]

HCGHCGGIRLHPTHYSIR [SEQ ID NO: 48]

HCGxCGGIRLHPTHYSIR [SEQ ID NO: 49]

CHGCYRQVPGSDP [SEQ ID NO: 50]

HCHGCYRQVPGSDP [SEQ ID NO: 51]

HCxGCYRQVPGSDP [SEQ ID NO: 52]

CHGCFVALCATDV [SEQ ID NO: 53]

HCHGCFVALCATDV [SEQ ID NO: 54]

HCxGCFVALCATDV [SEQ ID NO: 55]

CHGCFKELEGWEP [SEQ ID NO: 56]

HCHGCFKELEGWEP [SEQ ID NO: 57]

HCxGCFKELEGWEP [SEQ ID NO: 58]

CHGCVASSYAAAQ [SEQ ID NO: 59]

HCHGCVASSYAAAQ [SEQ ID NO: 60]

HCxGCVASSYAAAQ [SEQ ID NO: 61]

-continued

CHGCFNSNRANSS [SEQ ID NO: 62]

HCHGCFNSNRANSS [SEQ ID NO: 63]

HCxGCFNSNRANSS [SEQ ID NO: 64]

CGHCLVLAPTREL [SEQ ID NO: 65]

HCGHCLVLAPTREL [SEQ ID NO: 66]

HCGxCLVLAPTREL [SEQ ID NO: 67]

CGHCPEFLEQKRA [SEQ ID NO: 68]

HCGHCPEFLEQKRA [SEQ ID NO: 69]

HCGxCPEFLEQKRA [SEQ ID NO: 70]

CXXC [SEQ ID NO: 71]

CXXS [SEQ ID NO: 72]

CXXT [SEQ ID NO: 73]

SXXC [SEQ ID NO: 74]

TXXC [SEQ ID NO: 75]

XXXC [SEQ ID NO: 76]

CXXX [SEQ ID NO: 77]

HCXXX [SEQ ID NO: 78]

XXXCH [SEQ ID NO: 79]

HCXXC [SEQ ID NO: 80]

HCXXS [SEQ ID NO: 81]

HCXXT [SEQ ID NO: 82]

CXXCH [SEQ ID NO: 83]

SXXCH [SEQ ID NO: 84]

TXXCH [SEQ ID NO: 85]

HCXXCH [SEQ ID NO: 86]

XXXXLX [SEQ ID NO: 87]

DXXLL [SEQ ID NO: 88]

YXXX [SEQ ID NO: 89]

HX(0, 2)CXX[CST]:

H CXX[CST] [SEQ ID NO: 78]

HX CXX[CST] [SEQ ID NO: 90]

HXXCXX[CST] [SEQ ID NO: 91]

[CST]xxC(0, 2)H:

[CST]XXCH [SEQ ID NO: 79]

[CST]XxCXH [SEQ ID NO: 92]

[CST]XxCXXH [SEQ ID NO: 93]

CXXCX(0, 2)H:

CXXC H [SEQ ID NO: 83]

CXXCX H [SEQ ID NO: 94]

CXXCXXH [SEQ ID NO: 95]

H(0, 2)CXXC:

H CXXC [SEQ ID NO: 83]

H XCXXC [SEQ ID NO: 96]

HXXCXXC [SEQ ID NO: 97]

HX(0, 2)XCXXS:

H CXXS [SEQ ID NO: 81]

H XCXXS [SEQ ID NO: 98]

HXXCXXS [SEQ ID NO: 99]

HX(0, 2)XCXXT:

H CXXT [SEQ ID NO: 82]

H XCXXT [SEQ ID NO: 100]

HXXCXXT [SEQ ID NO: 101]

SXXCX(0, 2)H:

SXXC H [SEQ ID NO: 84]

SXXCX H [SEQ ID NO: 102]

SXXCXXH [SEQ ID NO: 103]

TXXCX(0, 2)H:

TXXC H [SEQ ID NO: 85]

TXXCX H [SEQ ID NO: 104]

TXXCXXH [SEQ ID NO: 105]

HCHXC [SEQ ID NO: 106]

CXXHCH [SEQ ID NO: 107]

H CPYCVRSLQPLALEGSLQKRG [SEQ ID NO: 108]

HAACPYCVRSLQPLALEGSLQKRG [SEQ ID NO: 109]

AHACPYCVRSLQPLALEGSLQKRG [SEQ ID NO: 110]

AAACPYCVRSLQPLALEGSLQKRG [SEQ ID NO: 111]

AAACHPCVRSLQPLALEGSLQKRG [SEQ ID NO: 112]

AAHCHPCVRSLQPLALEGSLQKRG [SEQ ID NO: 113]

AAACHGCVRSLQPLALEGSLQKRG [SEQ ID NO: 114]

HX CPYCSRVVHLYRNGKD [SEQ ID NO: 115]

HXXCPYCSRVVHLYRNGKD [SEQ ID NO: 116]

---

The invention claimed is:

1. An isolated immunogenic peptide of between 13 and 50 amino acids comprising
   (a) a human MHC class II T cell epitope of an antigen, said epitope having a length of between 8 and 16 amino acids that binds into the cleft of the human MHC class II molecule, and
   (b) a redox motif consisting of H-X(0,2)-C-X(2)-[CST] [SEQ ID NO: 78, 90 or 91] or [CST]-X(2)-C-X(0,2)-H [SEQ ID NO: 79, 92 or 93], wherein H is His, C is Cys, S is Ser, T is Thr and X is any amino acid,
   wherein said human MHC class II T cell epitope is immediately adjacent to said redox motif or separated from said redox motif by a linker of at most 7 amino acids,
   with the proviso that said antigen does not contain in its sequence said redox motif within a distance of 10 amino acids of said epitope.

2. The peptide according to claim 1, with the proviso that said antigen does not contain in its sequence said redox motif.

3. The peptide according to claim 1, wherein said redox motif is located N terminally from the human MHC class II T cell epitope.

4. The peptide according to claim 1, wherein said peptide has a length of between 13 and 30 amino acids.

5. The peptide according to claim 1, wherein the linker comprises at most 4 amino acids.

6. The peptide according to claim 1, wherein the MHC class II T cell epitope is separated from said redox motif by 2 amino acids.

7. The peptide according to claim 1, wherein X within the C-X(2)-[CST] (SEQ ID NO: 76) or [CST]-X(2)-C(SEQ ID NO: 77) sequence is Gly or Pro.

8. The peptide according to claim 1, wherein X within the C-X(2)-[CST] (SEQ ID NO: 76) or [CST]-X(2)-C(SEQ ID NO: 77) sequence is not Cys.

9. The peptide according to claim 1, wherein the at most 2 amino acids separating said histidine and said C-X(2)-[CST] (SEQ ID NO:76) or [CST]-X(2)-C (SEQ ID NO: 77) sequence do not comprise Cys, Ser or Thr.

10. The peptide according to claim 1, wherein the redox motif consisting of H-C-X(2)-[CST] [SEQ ID NO: 78] or [CST]-X(2)-C-H [SEQ ID NO: 79].

* * * * *